(12) United States Patent
Fukazawa

(10) Patent No.: US 12,136,196 B2
(45) Date of Patent: Nov. 5, 2024

(54) MEDICAL SYSTEM, INFORMATION PROCESSING DEVICE, AND INFORMATION PROCESSING METHOD

(71) Applicant: SONY GROUP CORPORATION, Tokyo (JP)

(72) Inventor: Kentaro Fukazawa, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 423 days.

(21) Appl. No.: 17/441,413

(22) PCT Filed: Mar. 13, 2020

(86) PCT No.: PCT/JP2020/011027
§ 371 (c)(1),
(2) Date: Sep. 21, 2021

(87) PCT Pub. No.: WO2020/203164
PCT Pub. Date: Oct. 8, 2020

(65) Prior Publication Data
US 2022/0188988 A1 Jun. 16, 2022

(30) Foreign Application Priority Data
Mar. 29, 2019 (JP) ................................ 2019-069135

(51) Int. Cl.
*G06T 5/70* (2024.01)
(52) U.S. Cl.
CPC ...... *G06T 5/70* (2024.01); *G06T 2207/10056* (2013.01); *G06T 2207/10068* (2013.01)

(58) Field of Classification Search
CPC .......... A61B 1/000095; A61B 1/00009; A61B 1/0005; A61B 5/0261; A61B 5/1128;
(Continued)

(56) References Cited

U.S. PATENT DOCUMENTS 7,460,689 B1 * 12/2008 Chan ....................... G06T 7/254
382/103
2006/0221253 A1 * 10/2006 Kai .......................... H04N 5/21
348/E5.077
(Continued)

FOREIGN PATENT DOCUMENTS

| CN | 102316247 A | 1/2012 |
|----|-------------|--------|
| CN | 104221361 A | 12/2014 |

(Continued)

OTHER PUBLICATIONS

International Search Report and Written Opinion of PCT Application No. PCT/JP2020/011027, issued on Jun. 9, 2020, 09 pages of ISRWO.

*Primary Examiner* — Chan S Park
*Assistant Examiner* — Oo C Rhim
(74) *Attorney, Agent, or Firm* — CHIP LAW GROUP

(57) ABSTRACT

A medical system includes a light source that irradiates an imaging target with light, an imaging device that images reflected light from the imaging target irradiated with the light, and a noise reduction processing means that acquires a plurality of images captured by the imaging device and performs noise reduction processing on one image of interest out of a plurality of images. The noise reduction processing means uses an image N (N is an integer not smaller than 2) frames before the image of interest as a reference image.

7 Claims, 15 Drawing Sheets

(58) Field of Classification Search
CPC .... A61B 1/045; H04N 23/6811; H04N 19/51; H04N 19/513; H04N 23/00; H04N 23/60; G06T 2207/10068; G06T 7/0012; G06T 5/50; G06T 2207/10064; G06T 2207/30004; G06T 2207/30101; G06T 2207/10016; G06T 5/002; G06T 2207/30096; G06T 7/248; G06T 7/246; G06T 7/254; G06T 1/0007; G06T 2207/20221; G06T 2207/30168; G06T 7/20; G06T 2207/10056; G06T 2207/20182

See application file for complete search history.

(56) References Cited

U.S. PATENT DOCUMENTS

| | | | |
|---|---|---|---|
| 2009/0169080 A1* | 7/2009 | Noordhoek | G06T 5/003 382/131 |
| 2010/0188535 A1* | 7/2010 | Mitsuya | H04N 1/2145 348/241 |
| 2010/0225790 A1* | 9/2010 | Sasaki | G06T 5/20 348/241 |
| 2011/0317043 A1* | 12/2011 | On | H04N 23/6811 348/241 |
| 2012/0262559 A1* | 10/2012 | On | A61B 1/000095 348/208.4 |
| 2013/0022268 A1 | 1/2013 | Kishima | |
| 2013/0084024 A1* | 4/2013 | Yokokawa | G06T 5/50 382/274 |
| 2013/0242198 A1* | 9/2013 | Lee | H04N 5/213 348/618 |
| 2014/0226726 A1* | 8/2014 | Yokokawa | H04N 19/55 375/240.16 |
| 2015/0042774 A1 | 2/2015 | Sugano et al. | |
| 2015/0085943 A1 | 3/2015 | Taniguchi et al. | |
| 2015/0262336 A1* | 9/2015 | Jin | G06T 5/50 382/107 |
| 2015/0279006 A1* | 10/2015 | Choi | G06T 7/223 382/264 |
| 2017/0064204 A1* | 3/2017 | Sapiro | H04N 23/6811 |
| 2018/0144443 A1* | 5/2018 | Tetsuka | H04N 5/21 |
| 2018/0330476 A1* | 11/2018 | Omori | G06T 5/50 |
| 2019/0050968 A1* | 2/2019 | Suzuki | G06T 1/20 |
| 2019/0287673 A1* | 9/2019 | Michihata | G16H 40/63 |
| 2020/0098104 A1* | 3/2020 | Kashima | H04N 7/18 |
| 2020/0375439 A1* | 12/2020 | Endo | A61B 1/000095 |

FOREIGN PATENT DOCUMENTS

| | | | | |
|---|---|---|---|---|
| JP | 2009044361 A | * | 2/2009 | |
| JP | 2009105533 A | * | 5/2009 | |
| JP | 2012010730 A | * | 1/2012 | G06T 5/002 |
| JP | 2012142866 A | * | 7/2012 | |
| JP | 2012151787 A | * | 8/2012 | |
| JP | 2012222510 A | * | 11/2012 | |
| JP | 2013025466 A | * | 2/2013 | G06T 5/002 |
| JP | 2013157755 A | * | 8/2013 | |
| JP | 2013-240039 A | | 11/2013 | |
| JP | 5603676 B2 | | 10/2014 | |
| JP | 2015029841 A | * | 2/2015 | A61B 1/00009 |
| JP | 2016192986 A | | 11/2016 | |
| JP | 2019101996 A | * | 6/2019 | |
| JP | 2019101997 A | * | 6/2019 | |
| WO | WO-2018123613 A1 | * | 7/2018 | A61B 1/00 |
| WO | WO-2018168261 A1 | * | 9/2018 | A61B 1/00009 |

* cited by examiner

FIG. 3
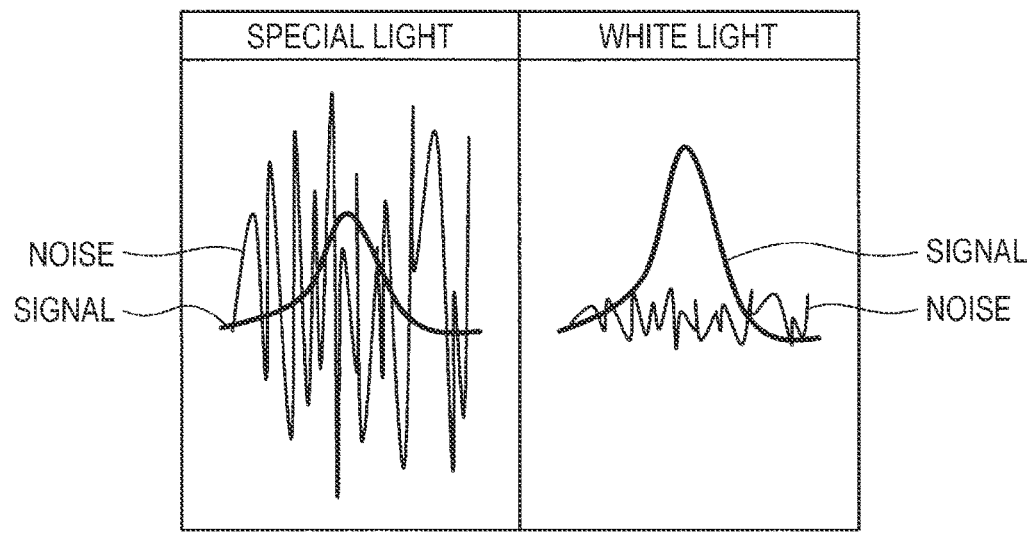
FIG. 4A
FIG. 4B
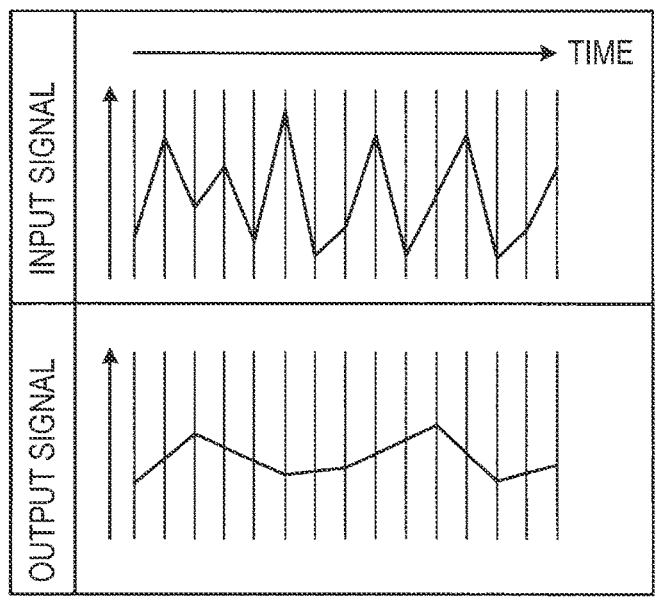

MEDICAL SYSTEM, INFORMATION PROCESSING DEVICE, AND INFORMATION PROCESSING METHOD

CROSS REFERENCE TO RELATED APPLICATIONS

This application is a U.S. National Phase of International Patent Application No. PCT/JP2020/011027 filed on Mar. 13, 2020, which claims priority benefit of Japanese Patent Application No. JP 2019-069135 filed in the Japan Patent Office on Mar. 29, 2019. Each of the above-referenced applications is hereby incorporated herein by reference in its entirety.

TECHNICAL FIELD

The present disclosure relates to a medical system, an information processing device, and an information processing method.

BACKGROUND ART

In general, a moving image obtained by imaging might include various types of noise. Therefore, it is desirable to perform noise reduction processing (NR processing) for reducing noise of the moving image. Furthermore, in a medical field, noise reduction of the moving image might be especially important due to the following circumstances.

In the medical field, for example, there is a case where a surgeon and the like visually recognizes a lesion and the like by viewing a moving image of a special light image captured by irradiating a living body with special light (for example, near-infrared light) having a specific wavelength band. However, the special light image captured with the special light having a narrower wavelength band than that of white light is generally darker than a white light image, so that an influence of noise becomes relatively large. Therefore, in the special light image, for example, there is a case where faint fluorescence in a deep portion of a living body by a predetermined drug is buried in noise and cannot be seen and the like. Then, the surgeon cannot make correct determination by viewing the image.

Therefore, the NR processing is required for such special light image. The NR processing mainly includes NR processing in a time direction and NR processing in a spatial direction. The NR processing in the time direction is known as a technology for efficiently reducing noise. In the NR processing in the time direction, for example, pixel values are averaged and the like in the time direction.

CITATION LIST

Patent Document

Patent Document 1: Japanese Patent No. 5603676

SUMMARY OF THE INVENTION

Problems to be Solved by the Invention

However, in the conventional NR processing in the time direction, magnitude of the noise itself becomes smaller, but a correlation of the noise becomes higher in the time direction and a frame rate (time variation) of the noise also becomes smaller depending on the type of the noise and the like. Then, in consideration of a visual characteristic of a human afterimage effect, a decrease in the frame rate of the noise might improve visibility of moving image noise.

Therefore, the present disclosure proposes a medical system, an information processing device, and an information processing method capable of more reliably decreasing the visibility of the moving image noise by performing the NR processing in the time direction on the image.

Solutions to Problems

In order to solve the above-described problem, a medical system according to an aspect of the present disclosure includes a light source that irradiates an imaging target with light, an imaging device that images reflected light from the imaging target irradiated with the light, and a noise reduction processing means that acquires a plurality of images captured by the imaging device and performs noise reduction processing on one image of interest out of a plurality of the images. The noise reduction processing means uses an image N (N is an integer not smaller than 2) frames before the image of interest as a reference image.

BRIEF DESCRIPTION OF DRAWINGS

FIG. 3 is a schematic diagram illustrating a relationship between signals of special light and white light and magnitude of noise according to the first embodiment of the present disclosure.

FIGS. 4A and 4B are graphs schematically illustrating temporal changes of an input signal and an output signal in a case where NR processing in a time direction is performed in a comparative example.

In the first embodiment of the present disclosure, in FIGS. 5A, 5B, 5C and 5D are graphs schematically illustrating temporal changes of an input signal, an output signal in a case of performing the NR processing only with even-numbered frames, an output signal in a case of performing the NR processing only with odd-numbered frames, and an actual output signal, respectively.

Figure 6:
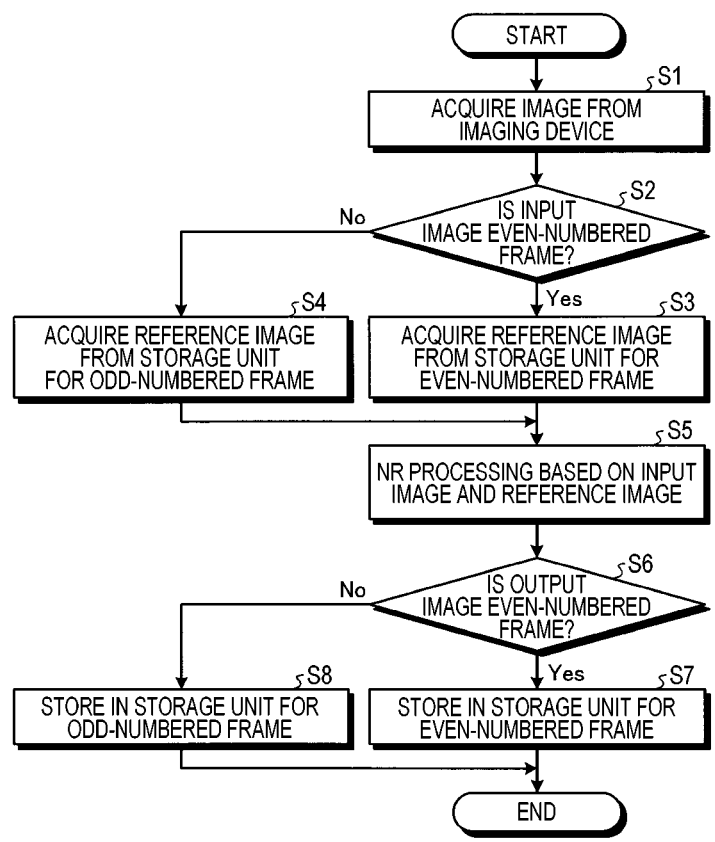

FIG. 6 is a flowchart illustrating image processing by the information processing device according to the first embodiment of the present disclosure.

Figure 7:
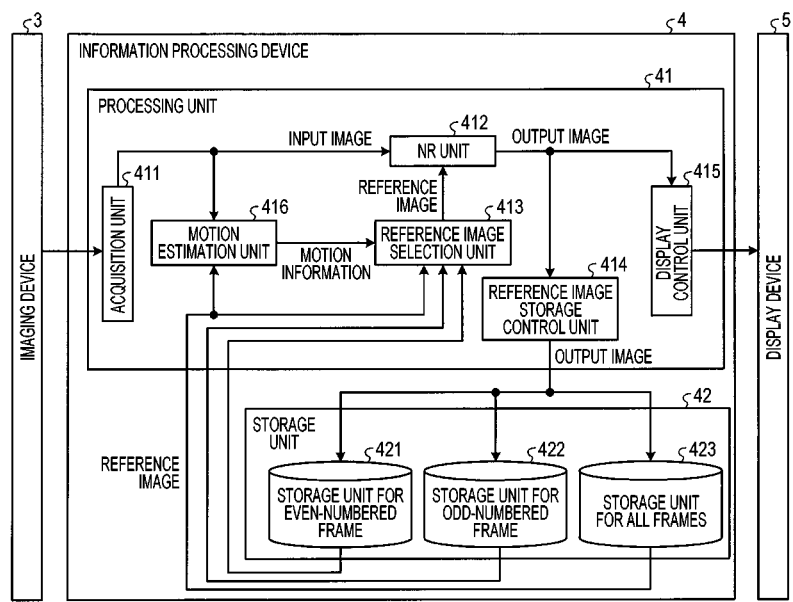

FIG. 7 is a view illustrating a configuration example of an information processing device according to a second embodiment of the present disclosure.

Figure 8:
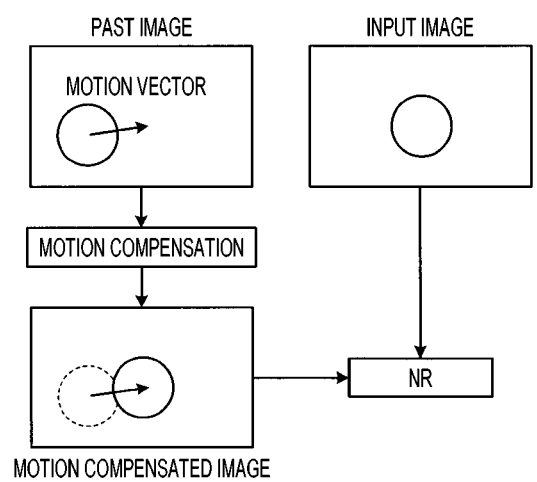

FIG. 8 is an explanatory view of motion compensation and noise reduction processing according to the second embodiment of the present disclosure.

Figure 9:
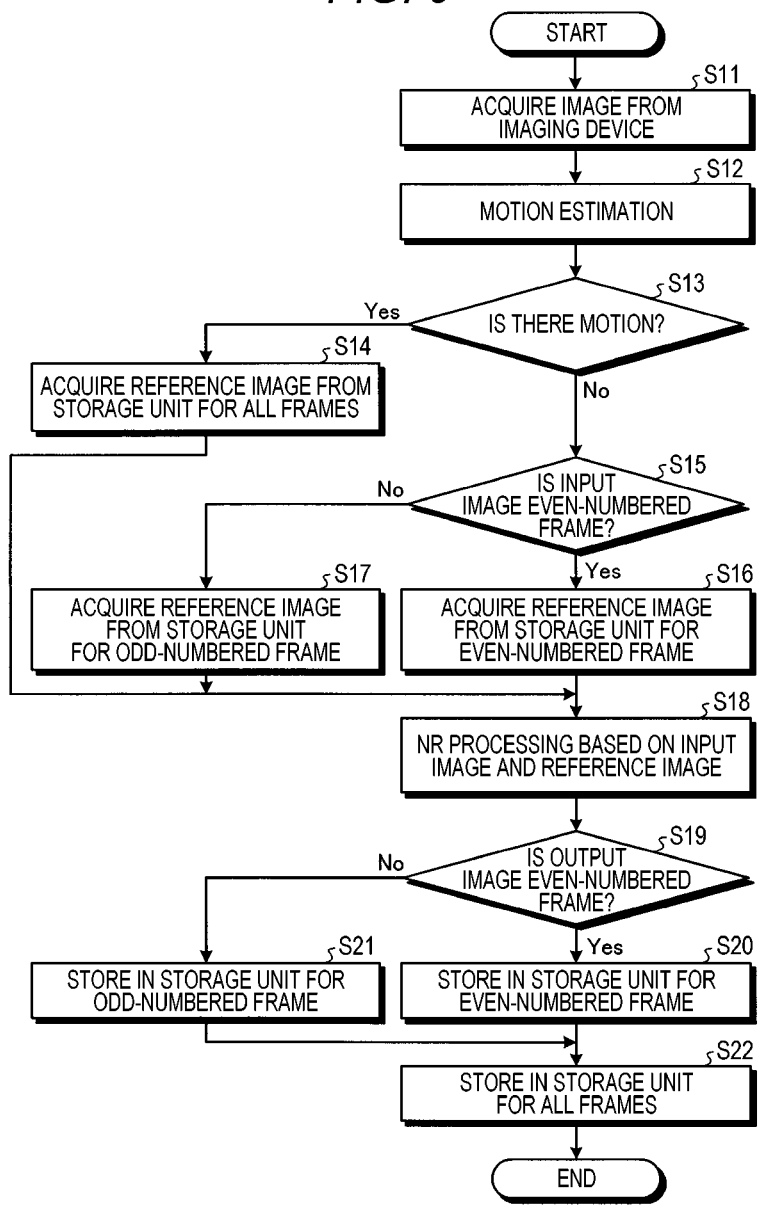

FIG. 9 is a flowchart illustrating image processing by the information processing device according to the second embodiment of the present disclosure.

Figure 10:
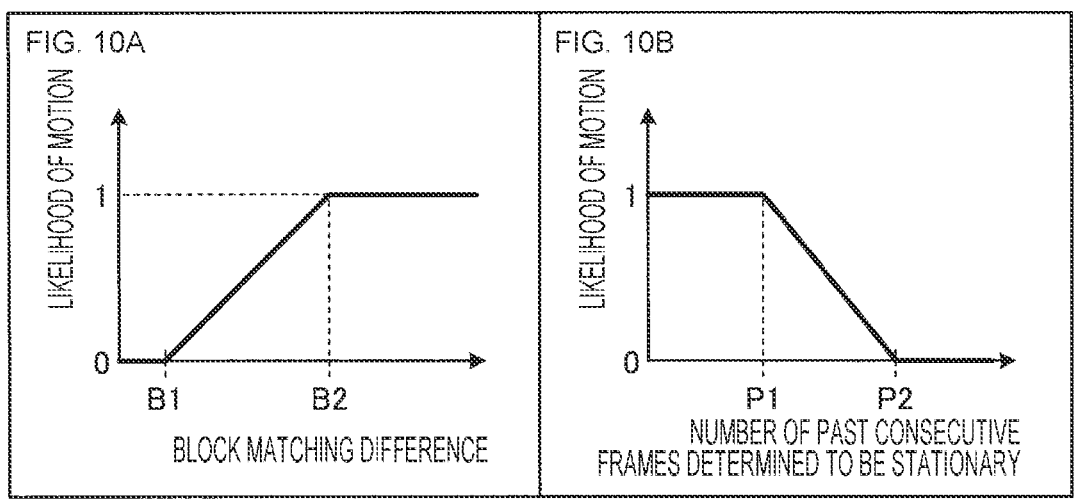

In the second embodiment of the present disclosure, in FIG. 10A, is a graph illustrating a relationship between likelihood of motion and a block matching difference, and FIG. 10B is a graph illustrating a relationship between the likelihood of motion and the number of past consecutive frames determined to be stationary.

Figure 11:
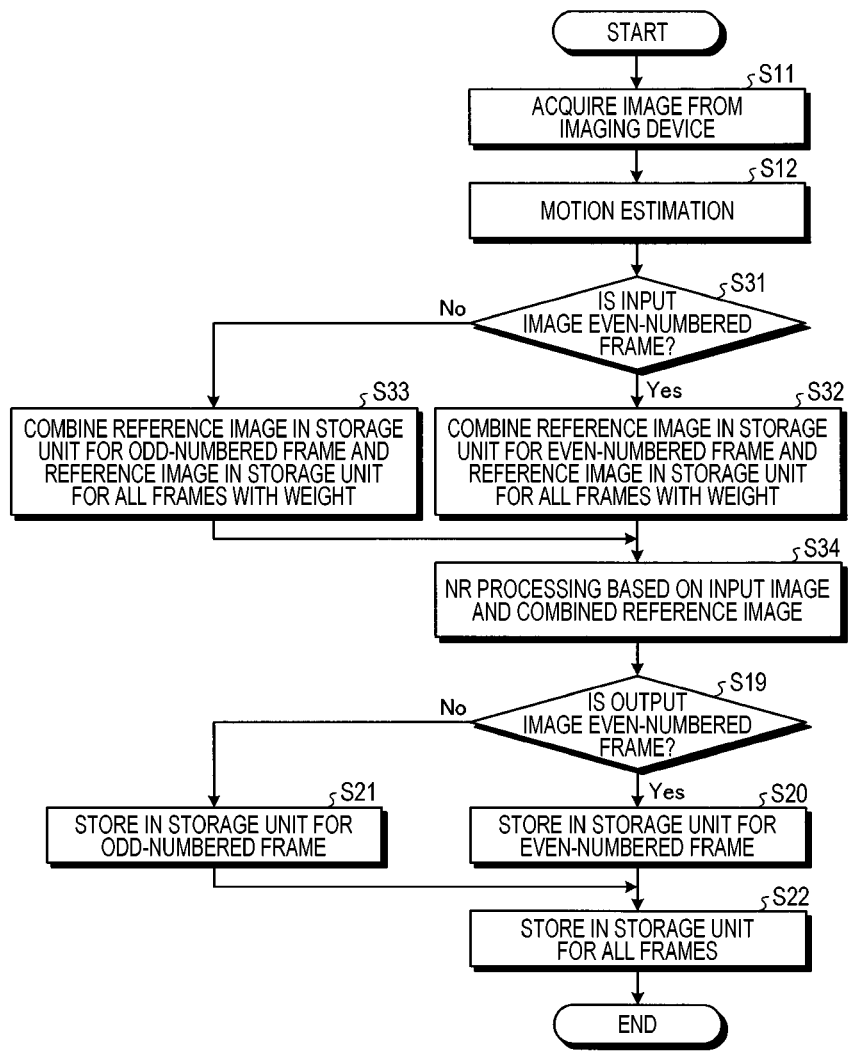

FIG. 11 is a flowchart illustrating image processing by an information processing device according to a third embodiment of the present disclosure.

Figure 12:

FIG. 12 is a view illustrating images of an input signal, in a method of a comparative example, and in first and second methods in the first embodiment of the present disclosure, and FFT results thereof.

Figure 13:
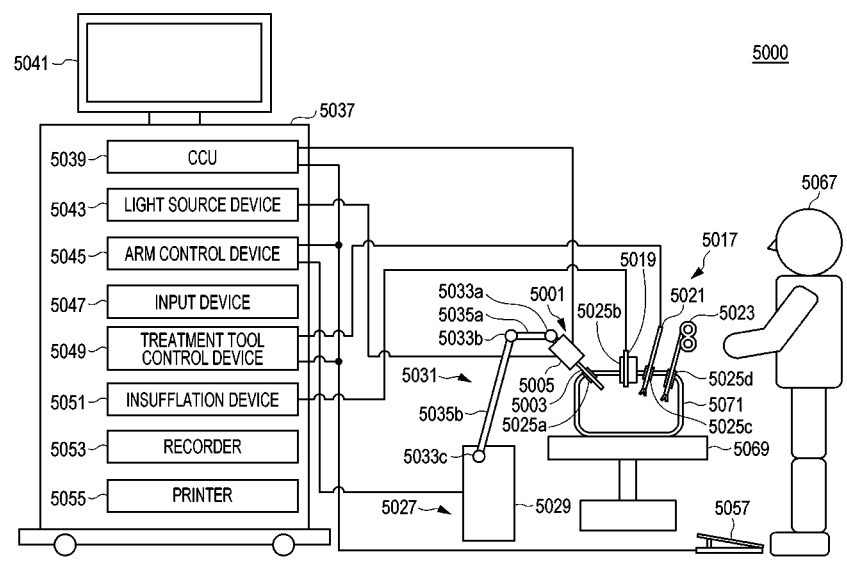

FIG. 13 is a view illustrating an example of a schematic configuration of an endoscopic surgery system according to an application example 1 of the present disclosure.

Figure 14:
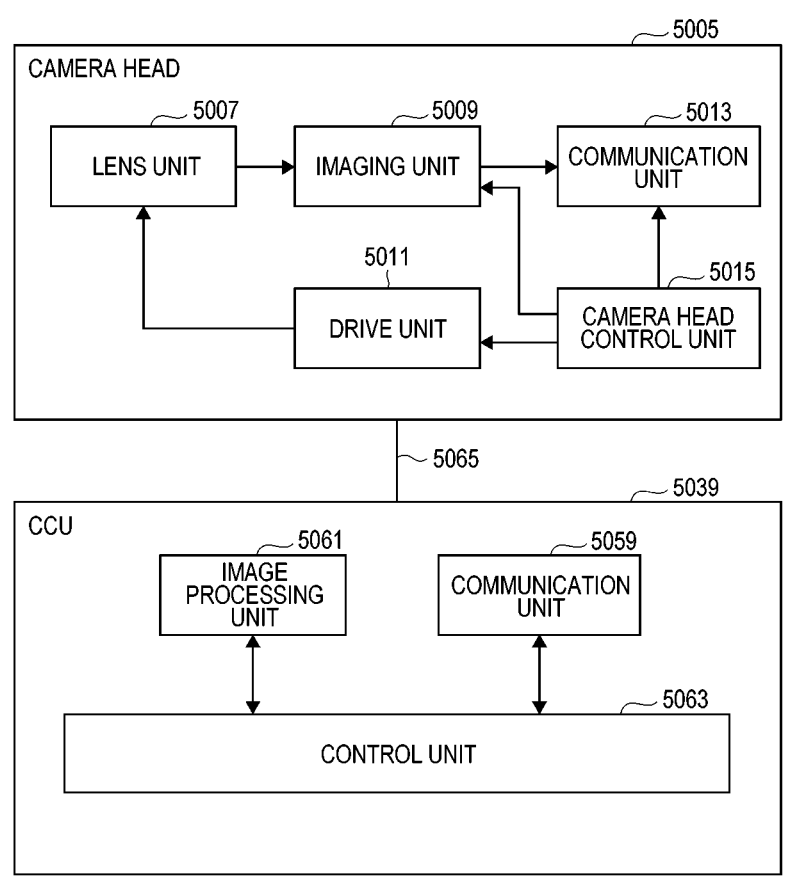

FIG. 14 is a block diagram illustrating an example of functional configurations of a camera head and a CCU illustrated in FIG. 13.

Figure 15:
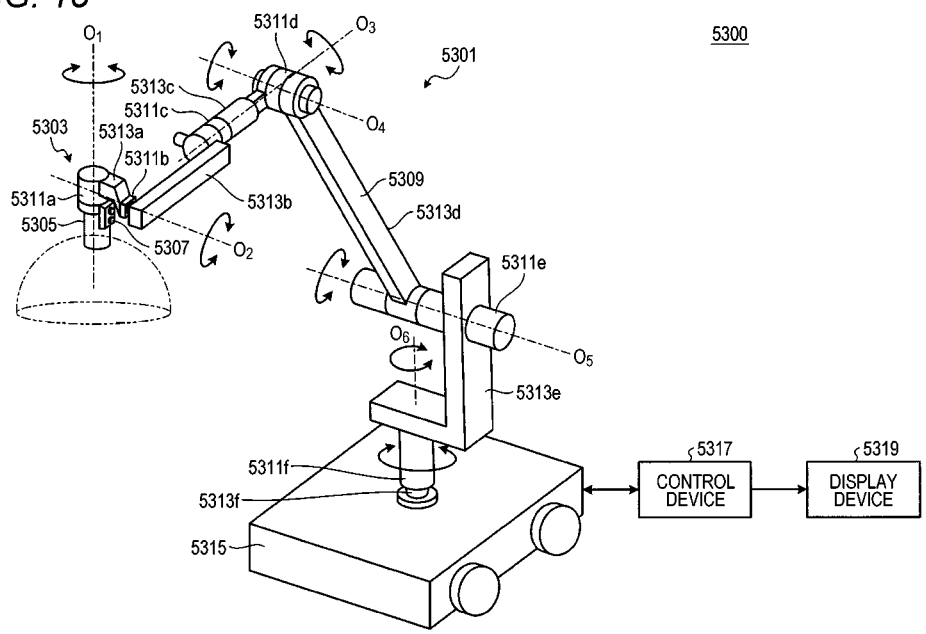

FIG. 15 is a view illustrating an example of a schematic configuration of a microscopic surgery system according to an application example 2 of the present disclosure.

Figure 16:
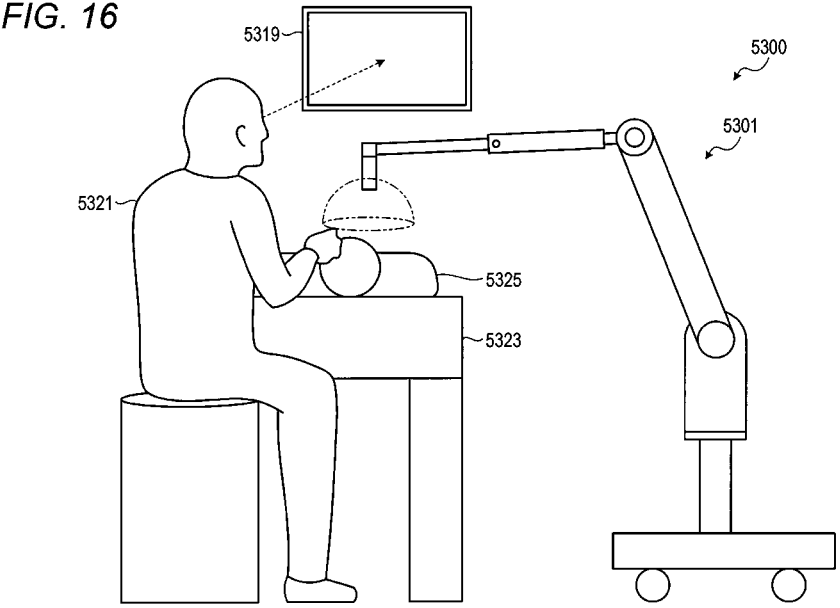

FIG. 16 is a view illustrating a state of surgery using the microscopic surgery system illustrated in FIG. 15.

MODE FOR CARRYING OUT THE INVENTION

Hereinafter, an embodiment of the present disclosure is described in detail with reference to the drawings. Note that, in each of the following embodiments, the same components are assigned with the same reference sign, and the description thereof is not repeated appropriately.

First Embodiment

Figure 1:
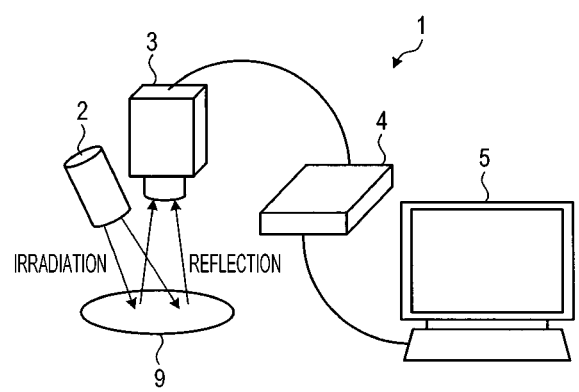
FIG. 1 is a view illustrating a configuration of a medical system according to a first embodiment of the present disclosure.

First, a first embodiment is described. FIG. 1 is a view illustrating a configuration of a medical system 1 according to a first embodiment of the present disclosure. The medical system 1 according to the first embodiment is roughly provided with at least a light source 2 (light source), an imaging device 3 (imaging device), and an information processing device 4. Furthermore, the medical system 1 may further be provided with a display device 5 and the like as necessary. Hereinafter, each component is described in detail.

(1) Light Source

The light source 2 irradiates an imaging target 9 with special light having a specific wavelength band (an example of light). The special light is, for example, near-infrared light.

(2) Imaging Target

The imaging target 9 may be various targets, and this is, for example, a living body. For example, by using the medical system 1 according to the present disclosure in microscopic surgery, endoscopic surgery and the like, it is possible to perform surgery while confirming a position of the blood vessel. Therefore, safer and more accurate surgery may be performed, and this may also contribute to further development of medical technology.

(3) Imaging Device

The imaging device 3 images reflected light from the imaging target 9 irradiated with the special light. The imaging device 3 is, for example, an infrared (IR) imager that captures a special light image.

(4) Information Processing Device

Figure 2:
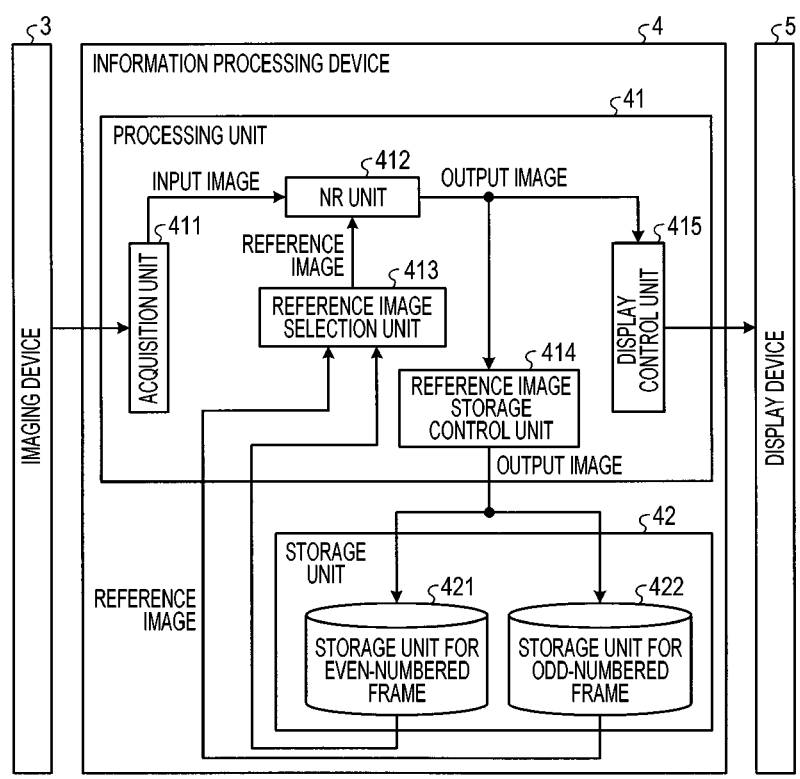
FIG. 2 is a view illustrating a configuration of an information processing device according to the first embodiment of the present disclosure.

Next, the information processing device 4 is described with reference to FIG. 2. FIG. 2 is a view illustrating a configuration of the information processing device 4 according to the first embodiment of the present disclosure. The information processing device 4 is an image processing device, and is provided with a processing unit 41 and a storage unit 42 as main components. Note that, hereinafter, out of functions of the information processing device 4, items related to the NR processing are mainly described, and description of various types of image signal processing for camera and the like other than the NR processing is appropriately omitted.

Furthermore, before describing the processing executed by the information processing device 4 in detail, an outline and a purpose of the processing executed by the information processing device 4 are described with reference to FIGS. 3, 4A, 4B, 5A, 5B, 5C and 5D. FIG. 3 is a schematic diagram illustrating a relationship between signals of the special light and white light and magnitude of noise according to the first embodiment of the present disclosure. As illustrated in FIG. 3, the signal obtained using the special light is relatively smaller than the signal obtained using the white light with respect to noise Therefore, in the special light image, for example, there is a case where faint fluorescence in a deep portion of a living body due to a predetermined drug is buried in noise and cannot be seen and the like. Then, the surgeon cannot make correct determination by viewing the image.

Therefore, it is conceivable to perform the NR processing in a time direction on the special light image. In the NR processing in the time direction, for example, pixel values are averaged and the like in the time direction.

Here, in FIGS. 4A, and 4B are graphs schematically illustrating temporal changes of an input signal and an output signal, respectively, in a case where the NR processing in the time direction is performed in a comparative example (conventional technology). Note that, in FIGS. 4A, and 4B the input signal and the output signal indicate only noise components other than an original normal signal.

In general, noise in a moving image includes fixed noise in which the magnitude of the noise does not change with time and variable noise in which the magnitude of the noise changes with time. Among them, the noise mainly targeted in this embodiment is the latter variable noise. Examples of the variable noise include so-called light shot noise generated by the imaging device 3 such as an infrared (IR) imager, electromagnetic wave noise caused by electromagnetic waves emitted from various electronic devices around the imaging device 3 and the like, for example.

In FIG. 4A, the input signal is the variable noise. Then, in the output signal in FIG. 4B obtained by performing the conventional NR processing in the time direction on the input signal in FIG. 4A, the magnitude of the noise itself becomes smaller than that of the input signal in FIG. 4A, but a correlation of the noise becomes high in the time direction, and a frame rate of the noise also becomes small.

Furthermore, it is considered that there is an afterimage effect of about 50 ms to 100 ms as a visual characteristic of a human. Therefore, in consideration of the visual characteristic of the afterimage effect of the human, a decrease in the frame rate of the noise might improve visibility of the moving image noise. Therefore, in a case where the NR unit 412 (to be described later in detail) performs the NR processing using an image N frames before (N is an integer not smaller than 2) as a reference image, N is preferably an integer not smaller than 2 satisfying following expression (1).

$$\text{(Time length between frames)} \times N \leq 100 \text{ ms} \quad \text{expression (1)}$$

For example, when the frame rate is 60 frames per second (fps), the time length between the frames is 50/3 ms, and N is preferably any integer of 2 to 6. Then, in the first embodiment, a case of N=2 is mainly described as an example.

Hereinafter, a frame (image) a frame number of which is an even number is sometimes referred to as an even-numbered frame, and a frame a frame number of which is an odd number is sometimes referred to as an odd-numbered frame.

In the first embodiment of the present disclosure, in FIGS. 5A, 5B, 5C and 5D are graphs schematically illustrating temporal changes of an input signal, an output signal in a case of performing the NR processing only with the even-numbered frames, an output signal in a case of performing the NR processing only with the odd-numbered frames, and an actual output signal, respectively. Furthermore, each signal in FIGS. 5A, 5B, 5C and 5D indicates only noise components other than an original normal signal as in the case in FIGS. 4A and 4B.

In the information processing device 4 of the first embodiment, in a case where the NR processing is performed in the time direction on one image of interest out of a plurality of images in time series, the NR processing is performed using an image two frames before as a reference image. In this case, for example, the NR processing is performed by performing weighted averaging on the image of interest and the reference image.

Then, the NR processing is performed on the input image of the even-numbered frame using an output image of the latest even-numbered frame as the image two frames before as the reference image. Furthermore, the NR processing is performed on the input image of the odd-numbered frame by using an output image of the latest odd-numbered frame as the image two frames before as the reference image.

Figure 5A:
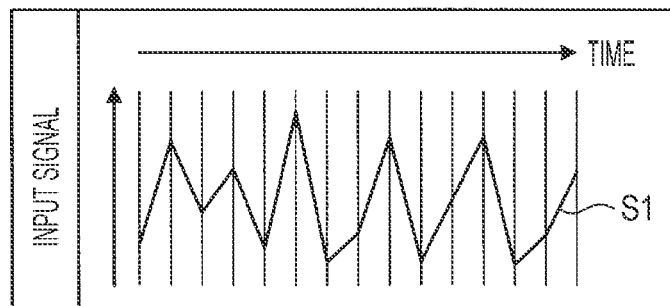
Figure 5B:
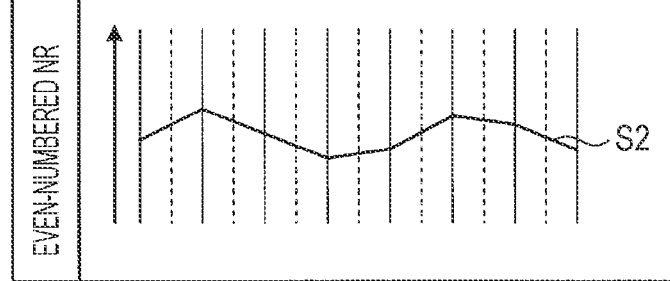
Figure 5C:
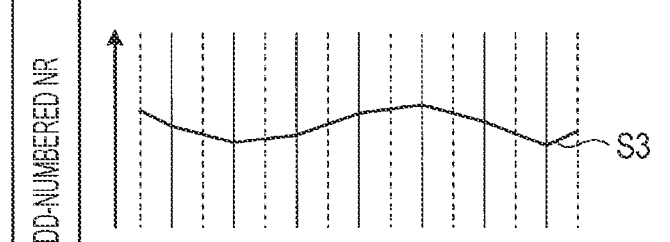

With respect to an input signal S1 illustrated in FIG. 5A, FIG. 5B illustrates an output signal S2 in a case of performing the NR processing only with the even-numbered frames, and FIG. 5C illustrates an output signal S3 in a case of performing the NR processing only on the odd-numbered frames. Then, FIG. 5D illustrates a case where the output signal S2 in FIG. 5B is adopted at a timing of the even-numbered frame and the output signal S3 in FIG. 5C is adopted at a timing of the odd-numbered frame as an actual output signal S4.

Figure 5D:
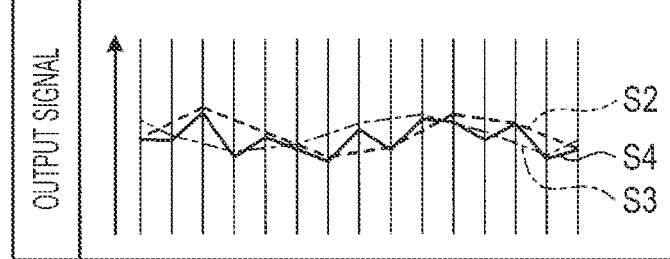

It may be understood that the frame rate of the noise of the output signal S4 in FIG. 5D does not decrease as compared with the output signal in FIG. 4B. Therefore, since the frame rate of the noise does not decrease, it is possible to avoid a situation in which visibility of the moving image noise is improved.

With reference to FIG. 2 again, processing executed by the information processing device 4 is described in detail. The processing unit 41 is realized by, for example, a central processing unit (CPU), and is provided with an acquisition unit 411, an NR unit 412 (noise reduction processing means), a reference image selection unit 413 (reference image selection means), a reference image storage control unit 414, and a display control unit 415.

The acquisition unit 411 acquires a plurality of images in time-series captured by the imaging device 3 that images the reflected light from the imaging target 9 irradiated with the special light.

The NR unit 412 performs the NR processing on one image of interest (input image) out of a plurality of images in time series in the time direction. In this case, the NR unit 412 performs the NR processing using the image N frames before (N is an integer not smaller than 2) as the reference image. The NR unit 412 performs the NR processing by performing weighted averaging on the image of interest (input image) and the reference image, for example.

The reference image selection unit 413 selects the reference image. Specifically, on the basis of the frame number of the input image, the reference image selection unit 413 selects the reference image from a storage unit for even-numbered frame 421 when the frame number is an even number, and selects the reference image from a storage unit for odd-numbered frame 422 when the frame number is an odd number.

The reference image storage control unit 414 controls a storage destination of the output image. Specifically, based on the frame number of the output image, the reference image storage control unit 414 stores the output image in the storage unit for even-numbered frame 421 when the frame number is the even number, and stores the output image in the storage unit for odd-numbered frame 422 when the frame number is the odd number.

The display control unit 415 performs control to display the special light image and the like subjected to the NR processing and the like on the display device 5.

The storage unit 42 stores various types of information such as the special light image acquired by the acquisition unit 411, a calculation result by each unit of the processing unit 41 and the like. Furthermore, the storage unit 42 is provided with the storage unit for even-numbered frame 421 and the storage unit for odd-numbered frame 422.

The storage unit for even-numbered frame 421 stores the reference image (output image) the frame number of which is the even number. The storage unit for odd-numbered frame 422 stores the reference image (output image) the frame number of which is the odd number. Note that, for example, it is sufficient that each of the storage unit for even-numbered frame 421 and the storage unit for odd-numbered frame 422 stores only the latest output image by overwriting, but there is no limitation. Furthermore, instead of the storage unit 42, a storage device outside the medical system 1 may be used.

(5) Display Device

Under control of the display control unit 415, the display device 5 displays various types of information such as the special light image acquired by the acquisition unit 411, a calculation result by each unit of the processing unit 41 and the like. Note that, a display device outside the medical system 1 may be used instead of the display device 5.

Next, image processing by the information processing device 4 is described with reference to FIG. 6. FIG. 6 is a flowchart illustrating the image processing by the information processing device 4 according to the first embodiment of the present disclosure.

At step S1, the acquisition unit 411 acquires an image (input image) from the imaging device 3 that images the reflected light from the imaging target 9 irradiated with the special light.

Next, at step S2, the processing unit 41 determines whether or not the input image is the even-numbered frame; in a case of Yes, the procedure shifts to step S3, and in a case of No, the procedure shifts to step S4.

At step S3, the reference image selection unit 413 acquires (selects) the reference image from the storage unit for even-numbered frame 421.

At step S4, the reference image selection unit 413 acquires (selects) the reference image from the storage unit for odd-numbered frame 422.

After steps S3 and S4, at step S5, the NR unit 412 performs the NR processing on the basis of the input image and the reference image.

Next, at step S6, the processing unit 41 determines whether or not the output image is the even-numbered frame; in a case of Yes, the procedure shifts to step S7, and in a case of No, the procedure shifts to step S8.

At step S7, the reference image storage control unit 414 stores the output image in the storage unit for even-numbered frame 421.

At step S8, the reference image storage control unit 414 stores the output image in the storage unit for odd-numbered frame 422.

Furthermore, after steps S7 and S8, the display control unit 415 performs control to allow the display device 5 to display the special light image and the like after the NR processing according to an operation and the like by a user.

In this manner, according to the information processing device 4 of the first embodiment, in a case where the NR processing is performed on the input image in the time direction, by performing the NR processing using the image two frames before (an example of the N frames before) as the reference image, even if the magnitude of the noise itself decreases, the frame rate of the noise does not decrease, and the visibility of the moving image noise may be more surely decreased.

For example, in a neurosurgical operation, a cardiac surgery operation and the like, fluorescence observation using indocyanine green (ICG) is generally performed for blood flow observation at the time of surgery. This is a method of minimally invasively observing running of the blood vessel or the lymphatic vessel by utilizing a feature that ICG binds to plasma protein in vivo and emits fluorescence by near-infrared excitation light. In this case, according to the information processing device 4 of the first embodiment, in a case where the NR processing is performed in the time direction on the special light image with a relatively larger influence of the noise than that with the white light image, the frame rate of the noise does not decrease, and the visibility of the moving image noise may be more reliably decreased. Therefore, a possibility that the surgeon makes erroneous determination when viewing the special light image after the NR processing decreases, and the surgery may be performed more safely. Such a function effect and the like are described later in detail in application examples 1 and 2 below.

Second Embodiment

Next, a second embodiment is described. Description of matters similar to those of the first embodiment is omitted as appropriate. In the first embodiment, when the NR processing in the time direction is performed, the output image N frames before is used as the reference image regardless of temporal motion in the input image (for example, the motion due to heartbeat, body motion and the like in the living body that is the imaging target 9). In contrast, in the second embodiment, an output image N frames before and an output image one frame before are selectively used as a reference image on the basis of temporal motion in an input image.

FIG. 7 is a view illustrating a configuration example of an information processing device 4 according to the second embodiment of the present disclosure. The information processing device 4 in FIG. 7 is different from the information processing device 4 in FIG. 2 in that a processing unit 41 is provided with a motion estimation unit 416 (motion estimation means), and a storage unit 42 is provided with a storage unit for all frames 423.

The motion estimation unit 416 calculates a motion vector between a plurality of images on the basis of a feature amount in the image. Note that, a specific method of motion estimation by the motion estimation unit 416 may be, for example, block (template) matching or a gradient method, but is not limited thereto, and may be any method. Furthermore, the motion estimation may be performed in units of pixels or in units of blocks (group of pixels).

For example, the motion estimation unit 416 may determine that there is motion when a block matching difference (a value of a difference by block matching) is equal to or larger than a first threshold, and that there is no motion when the block matching difference is smaller than the first threshold.

Furthermore, the motion estimation unit 416 may determine that there is the motion when the number of past consecutive frames determined to be stationary (the number of frames consecutively determined to be stationary in the past) is smaller than a second threshold, and that there is no motion when the number of past consecutive frames determined to be stationary is equal to or larger than the second threshold. This is a statistical method.

The storage unit for all frames 423 stores all the reference images (output images). Note that, for example, it is sufficient that the storage unit for all frames 423 stores only the latest output image by overwriting, but there is no limitation.

In a case where the NR processing is performed on the image of interest (input image) in the time direction, a NR unit 412 performs the NR processing using at least one of the image N frames before or the image one frame before as the reference image according to magnitude of a motion vector calculated by the motion estimation unit 416.

More specifically, for example, the NR unit 412 performs the NR processing using the image one frame before as the reference image in a case where the magnitude of the motion vector is equal to or larger than a predetermined threshold (for example, in a case where it is determined that there is motion), and performs the NR processing using the image N frames before as the reference image in a case where the magnitude of the motion vector is smaller than the predetermined threshold (for example, in a case where it is determined that there is no motion).

Here, FIG. 8 is an explanatory view of motion compensation and noise reduction processing according to the second embodiment of the present disclosure. The NR unit 412 may perform the NR processing using a motion compensated image obtained by performing the motion compensation on the past image (output image one or more frames before) and the input image.

Next, the image processing by the information processing device 4 according to the second embodiment is described with reference to FIG. 9. FIG. 9 is a flowchart illustrating the image processing by the information processing device 4 according to the second embodiment of the present disclosure.

At step S11, an acquisition unit 411 acquires an image (input image) from an imaging device 3 that images the reflected light from the imaging target 9 irradiated with the special light.

Next, at step S12, the motion estimation unit 416 calculates a motion vector between a plurality of images on the basis of a feature amount in the image.

Next, at step S13, the motion estimation unit 416 determines whether or not there is the motion; in a case of Yes, the procedure shifts to step S14, and in a case of No, the procedure shifts to step S15.

At step S14, a reference image selection unit 413 acquires (selects) the reference image from the storage unit for all frames 423.

At step S15, the processing unit 41 determines whether or not the input image is an even-numbered frame; in a case of Yes, the procedure shifts to step S16, and in a case of No, the procedure shifts to step S17.

At step S16, the reference image selection unit 413 acquires (selects) the reference image from a storage unit for even-numbered frame 421.

At step S17, the reference image selection unit 413 acquires (selects) the reference image from a storage unit for odd-numbered frame 422.

After steps S14, S16, and S17, at step S18, the NR unit 412 performs the NR processing on the basis of the input image and the reference image. In a case where the procedure passes through step S14, the NR unit 412 performs the NR processing on the basis of the input image and the reference image after performing the motion compensation described above.

Next, at step S19, the processing unit 41 determines whether or not the output image is the even-numbered frame; in a case of Yes, the procedure shifts to step S20, and in a case of No, the procedure shifts to step S21.

At step S20, a reference image storage control unit 414 stores the output image in the storage unit for even-numbered frame 421.

At step S21, the reference image storage control unit 414 stores the output image in the storage unit for odd-numbered frame 422.

After steps S20 and S21, at step S22, the reference image storage control unit 414 stores the output image in the storage unit for all frames 423.

Furthermore, after step S22, the display control unit 415 performs control to allow a display device 5 to display a special light image and the like after the NR processing according to an operation and the like by a user.

In this manner, according to the information processing device 4 of the second embodiment, in a case of performing the NR processing on the input image in the time direction, by performing the NR processing by selectively using the image two frames before (an example of the N frames before) and the image one frame before as the reference image according to a result of the motion estimation, it is possible to flexibly support also in a case where there is the motion.

That is, for example, when the image two frames before is used as the reference image even in a case where there is the motion, the magnitude of the motion vector of a moving subject becomes larger than that of the image one frame before, and a difficulty level of the motion estimation and motion compensation, a calculation cost and the like might increase; however, such a situation may be avoided.

Third Embodiment

Next, a third embodiment is described. Description of matters similar to those of the second embodiment is omitted as appropriate. In the second embodiment, presence or absence of motion is determined in units of pixels or in units of blocks in the image. In contrast, in the third embodiment, the motion is determined with multiple values of "1" (present) to "0" (absent) in units of pixels or in units of blocks in the image.

In the third embodiment of the present disclosure, in FIGS. 10A and 10B, FIG. 10A is a graph illustrating a relationship between likelihood of motion and a block matching difference, and FIG. 10B is a graph illustrating a relationship between the likelihood of motion and the number of past consecutive frames determined to be stationary.

In FIG. 10A, the likelihood of motion is plotted along the ordinate, and the block matching difference is plotted along the abscissa. The likelihood of motion is "0" when the block matching difference is equal to or larger than 0 and smaller than B1, "1" when the block matching difference is equal to or larger than B2, and a value that linearly changes between "0" and "1" when the block matching difference is equal to or larger than B1 and smaller than B2.

In FIG. 10B, the likelihood of motion is plotted along the ordinate, and the number of past consecutive frames determined to be stationary is plotted along the abscissa. The likelihood of motion is "1" when the number of past consecutive frames determined to be stationary is equal to or larger than 0 and smaller than P1, "0" when the number of past consecutive frames determined to be stationary is equal to or larger than P2, and a value that linearly changes between "1" and "0" when the number of past consecutive frames determined to be stationary is equal to or larger than P1 and smaller than P2. This is a statistical method. Furthermore, linear is an example, and may be non-linear.

Then, a reference image selection unit 413 (FIG. 7) combines an image N frames before and an image one frame before with a weight (for example, when the likelihood of motion is $\alpha$, "1-$\alpha$":"$\alpha$") according to the likelihood of motion (the magnitude of the motion vector) to create a combined reference image. A NR unit 412 performs the NR processing after performing the motion compensation using the combined reference image.

Next, image processing by an information processing device 4 according to the third embodiment is described with reference to FIG. 11. FIG. 11 is a flowchart illustrating the image processing by the information processing device 4 according to the third embodiment of the present disclosure.

At step S11, an acquisition unit 411 acquires an image (input image) from an imaging device 3 that images the reflected light from the imaging target 9 irradiated with the special light.

Next, at step S12, a motion estimation unit 416 estimates motion between a plurality of images (calculates the motion vector) on the basis of a feature amount in the image.

Next, at step S31, a processing unit 41 determines whether or not the input image is an even-numbered frame; in a case of Yes, the procedure shifts to step S32, and in a case of No, the procedure shifts to step S33.

At step S32, the reference image selection unit 413 creates the combined reference image by combining the reference image (the image N frames before) in a storage unit for even-numbered frame 421 and the reference image (the image one frame before) in a storage unit for all frames 423 with a weight according to the likelihood of motion (the magnitude of the motion vector).

At step S33, the reference image selection unit 413 creates the combined reference image by combining the reference image (the image N frames before) in a storage unit for odd-numbered frame 422 and the reference image (the image one frame before) in the storage unit for all frames 423 with a weight according to the likelihood of motion (the magnitude of the motion vector).

After steps S32 and S33, at step S34, the NR unit 412 performs the NR processing after performing the motion compensation on the basis of the input image and the reference image. Since steps S19 to S22 are similar to those in FIG. 9, description thereof is omitted.

As described above, according to the information processing device 4 of the third embodiment, the motion in the image is determined with multiple values of "1" (present) to "0" (absent), and the reference image N frames before and the image one frame before are combined (blended) according to a determination result to be used for the NR processing, so that it is possible to more flexibly support the motion in the image, and further improve accuracy of the NR processing.

FFT Result by Experiment

Next, a fast Fourier transform (FFT) result of a comparative example by an experiment and the first embodiment is described with reference to FIG. 12. FIG. 12 is a view illustrating images of an input signal, in a method of the comparative example, and in first and second methods in the first embodiment of the present disclosure, and FFT results thereof. Note that, FIG. 12 illustrates only noise components other than an original normal signal as in the case in FIGS. 4A, 4B, 5A, and 5B.

The input signal illustrated in FIG. 12($a1$) indicates pixel values of the input signals of one predetermined line in a vertical direction (ordinate) out of the input signals corresponding to a rectangular image together with a lapse of time (abscissa). Note that, in ($b1$), ($c1$), and ($d1$) also, the ordinate and the abscissa are similar to those in ($a1$).

Then, FIG. 12($b1$) illustrates a result in a case of performing cyclic NR processing in a time direction on the input signal illustrated in FIG. 12($a1$) using the reference image one frame before by the method of the comparative example (conventional technology).

Furthermore, FIG. 12($c1$) illustrates a result in a case of performing the cyclic NR processing in the time direction on the input signal illustrated in FIG. 12($a1$) using the reference image two frames before by the first method of the first embodiment.

Furthermore, FIG. 12($d1$) illustrates a result in a case of performing the cyclic NR processing in the time direction on the input signal illustrated in FIG. 12($a1$) using the reference image three frames before by the second method of the first embodiment.

Furthermore, results of analyzing the images illustrated in FIGS. 12($a1$) to ($d1$) by FFT are as illustrated in FIGS. 12($a2$) to ($d2$). In FIGS. 12($a2$) to ($d2$), one predetermined line in the vertical direction is plotted along the ordinate as in FIGS. 12($a1$) to ($d1$), and a frequency (lower in center and higher on both ends) is plotted along the abscissa. Furthermore, in FIGS. 12($a2$) to ($d2$), black indicates "not applicable", and stronger white indicates larger degree of application.

In FIG. 12($a2$), it is dispersed from a high frequency to a low frequency. In contrast, in FIG. 12($b2$), there is an inclination to low frequency. That is, in the method of the comparative example (conventional technology), a frame rate of noise significantly decreases because the reference image one frame before is used in the NR processing.

Furthermore, in FIG. 12($c2$), it is dispersed into three of two high frequencies (around ½ of a sampling frequency) and low frequency. That is, in the first method of the first embodiment, it is understood that the decrease in the frame rate of noise is significantly suppressed as compared to that in the method of the comparative example because the reference image two frames before is used in the NR processing.

Furthermore, in FIG. 12($d2$), it is dispersed into three of two high frequencies (around ⅓ of the sampling frequency) and low frequency. That is, in the second method of the first embodiment, it is understood that the decrease in the frame rate of noise is significantly suppressed as compared to that in the method of the comparative example because the reference image three frames before is used in the NR processing.

Application Example 1

The technology according to the present disclosure may be applied to various products. For example, the technology according to the present disclosure may be applied to an endoscope system. Hereinafter, an endoscopic surgery system as an example of the endoscope system is described.

FIG. 13 is a view illustrating an example of a schematic configuration of an endoscopic surgery system 5000 to which the technology according to the present disclosure is applicable. FIG. 13 illustrates a state in which an operator (surgeon) 5067 performs surgery on a patient 5071 on a patient bed 5069 by using the endoscopic surgery system 5000. As illustrated, the endoscopic surgery system 5000 includes an endoscope 5001, other surgical tools 5017, a support arm device 5027 that supports the endoscope 5001, and a cart 5037 on which various devices for endoscopic surgery are mounted.

In the endoscopic surgery, a plurality of tubular hole opening tools referred to as trocars 5025$a$ to 5025$d$ is tapped into the abdominal wall instead of incising the abdominal wall to open the abdomen. Then, a lens tube 5003 of the endoscope 5001 and the other surgical tools 5017 are inserted into the body cavity of the patient 5071 from the trocars 5025$a$ to 5025$d$. In the illustrated example, an insufflation tube 5019, an energy treatment tool 5021, and forceps 5023 are inserted into the body cavity of the patient 5071 as the other surgical tools 5017. Furthermore, the energy treatment tool 5021 is a treatment tool that performs incision and exfoliation of tissue, sealing of the blood vessel or the like by high-frequency current and ultrasonic vibration. Note that, the illustrated surgical tools 5017 are merely an example, and various surgical tools generally used in the endoscopic surgery, such as tweezers, a retractor and the like, for example, may be used as the surgical tools 5017.

An image of a surgical site in the body cavity of the patient 5071 captured by the endoscope 5001 is displayed on a display device 5041. The operator 5067 performs a procedure such as resection of an affected site, for example, by using the energy treatment tool 5021 and the forceps 5023 while viewing the image of the surgical site displayed on the display device 5041 in real time. Note that, although not illustrated, the insufflation tube 5019, the energy treatment tool 5021, and the forceps 5023 are supported by the operator 5067, an assistant or the like during the surgery.

Support Arm Device

The support arm device 5027 is provided with an arm 5031 extending from a base 5029. In the illustrated example, the arm 5031 includes joints 5033$a$, 5033$b$, and 5033$c$, and links 5035$a$ and 5035$b$, and is driven by control by an arm control device 5045. The arm 5031 supports the endoscope 5001 and controls its position and attitude. Therefore, stable position fixing of the endoscope 5001 may be realized.

Endoscope

The endoscope 5001 includes the lens tube 5003 a region of a predetermined length from a distal end of which is inserted into the body cavity of the patient 5071, and a camera head 5005 connected to a proximal end of the lens tube 5003. In the illustrated example, the endoscope 5001 configured as a so-called rigid scope including a rigid lens tube 5003 is illustrated, but the endoscope 5001 may also be configured as a so-called flexible scope including a flexible lens tube 5003.

At the distal end of the lens tube 5003, an opening into which an objective lens is fitted is provided. A light source device 5043 is connected to the endoscope 5001 and light generated by the light source device 5043 is guided to the distal end of the lens tube by a light guide extending inside the lens tube 5003, and applied to an observation target in the body cavity of the patient 5071 via an objective lens. Note that, the endoscope 5001 may be a forward-viewing endoscope, an oblique-viewing endoscope, or a side-viewing endoscope.

An optical system and an imaging element are provided inside the camera head 5005, and reflected light (observation light) from the observation target is condensed on the imaging element by the optical system. The observation light is photoelectrically converted by the imaging element, and an electric signal corresponding to the observation light, that is, an image signal corresponding to an observation image is generated. The image signal is transmitted as RAW data to a camera control unit (CCU) 5039. Note that, the camera head 5005 has a function of adjusting magnification and a focal distance by appropriately driving the optical system thereof.

Note that, the camera head 5005 may be provided with a plurality of imaging elements in order to support, for example, stereoscopic vision (3D display) and the like. In this case, a plurality of relay optical systems is provided inside the lens tube 5003 in order to guide the observation light to each of the plurality of imaging elements.

Various Devices Mounted on Cart

The CCU 5039 includes a central processing unit (CPU), a graphics processing unit (GPU) and the like, and comprehensively controls operations of the endoscope 5001 and the display device 5041. Specifically, the CCU 5039 applies various types of image processing for displaying an image based on the image signal such as, for example, development processing (demosaic processing) to the image signal received from the camera head 5005. The CCU 5039 provides the image signal subjected to the image processing to the display device 5041. Furthermore, the CCU 5039 transmits a control signal to the camera head 5005, and controls drive thereof. The control signal may include information regarding an imaging condition such as the magnification, focal distance and the like.

The display device 5041 displays the image based on the image signal subjected to the image processing by the CCU 5039 under control of the CCU 5039. In a case where the endoscope 5001 supports high-resolution imaging such as 4K (3840 horizontal pixels×2160 vertical pixels), 8K (7680 horizontal pixels×4320 vertical pixels) or the like, and/or supports 3D display, for example, a device capable of performing high-resolution display and/or a device capable of performing 3D display may be used as the display device 5041, respectively, so as to support them. In a case of supporting the high-resolution imaging such as 4K, 8K or the like, by using the display device 5041 having a size of 55 inches or larger, a more immersive feeling may be obtained. Furthermore, a plurality of display devices 5041 having different resolutions and sizes may be provided depending on applications.

The light source device 5043 includes a light source such as, for example, a light emitting diode (LED), and supplies the endoscope 5001 with irradiation light when imaging the surgical site.

The arm control device 5045 includes a processor such as a CPU, for example, and operates according to a predetermined program to control drive of the arm 5031 of the support arm device 5027 according to a predetermined control method.

An input device 5047 is an input interface to the endoscopic surgery system 5000. A user may input various types of information and instructions to the endoscopic surgery system 5000 via the input device 5047. For example, the user inputs various types of information regarding the surgery such as physical information of the patient, information regarding a surgical procedure and the like via the input device 5047. Furthermore, for example, the user inputs an instruction to drive the arm 5031, an instruction to change the imaging condition by the endoscope 5001 (a type of the irradiation light, the magnification, focal distance and the like), an instruction to drive the energy treatment tool 5021 and the like via the input device 5047.

A type of the input device 5047 is not limited, and the input device 5047 may be various well-known input devices. As the input device 5047, for example, a mouse, a keyboard, a touch panel, a switch, a foot switch 5057, and/or a lever may be applied. In a case where the touch panel is used as the input device 5047, the touch panel may be provided on a display surface of the display device 5041.

Alternatively, the input device 5047 is a device worn by the user such as an eyeglass-type wearable device, a head-mounted display (HMD) and the like, for example, and various inputs are performed in accordance with a user's gesture and line-of-sight detected by these devices. Furthermore, the input device 5047 includes a camera capable of detecting motion of the user, and performs various inputs in accordance with the user's gesture and line-of-sight detected from a video imaged by the camera. Moreover, the input device 5047 includes a microphone capable of collecting user's voice, and various inputs are performed by audio via the microphone. In this manner, the input device 5047 is configured to be able to input various types of information in a contactless manner, so that especially the user belonging to a clean area (for example, the operator 5067) may operate a device belonging to an unclean area in a contactless manner. Furthermore, since the user may operate the device without releasing his/her hand from the surgical tool in use, convenience for the user is improved.

A treatment tool control device 5049 controls drive of the energy treatment tool 5021 for cauterization and incision of tissue, sealing of the blood vessel or the like. An insufflation device 5051 injects gas into the body cavity via the insufflation tube 5019 to inflate the body cavity of the patient 5071 for the purpose of securing a visual field by the endoscope 5001 and securing a working space of the operator. A recorder 5053 is a device capable of recording various types of information regarding the surgery. A printer 5055 is a device capable of printing various types of information regarding the surgery in various formats such as text, image, graph or the like.

Hereinafter, a particularly characteristic configuration in the endoscopic surgery system 5000 is described in further detail.

Support Arm Device

The support arm device 5027 is provided with the base 5029 as a base, and the arm 5031 extending from the base 5029. In the illustrated example, the arm 5031 includes a plurality of joints 5033a, 5033b, and 5033c, and a plurality of links 5035a and 5035b connected by the joint 5033b, but in FIG. 13, for simplicity, the configuration of the arm 5031 is illustrated in a simplified manner. Actually, shapes, the number, and arrangement of the joints 5033a to 5033c and the links 5035a and 5035b, directions of rotational axes of the joints 5033a to 5033c and the like may be appropriately set so that the arm 5031 has a desired degree of freedom. For example, the arm 5031 may be preferably configured with six or more degrees of freedom. Therefore, since it becomes possible to feely move the endoscope 5001 within a movable range of the arm 5031, the lens tube 5003 of the endoscope 5001 may be inserted into the body cavity of the patient 5071 in a desired direction.

Each of the joints 5033a to 5033c is provided with an actuator, and each of the joints 5033a to 5033c is configured to be rotatable around a predetermined rotational axis by drive of the actuator. The drive of the actuator is controlled by the arm control device 5045, so that rotation angles of the respective joints 5033a to 5033c are controlled, and the drive of the arm 5031 is controlled. Therefore, control of the position and attitude of the endoscope 5001 may be realized. At that time, the arm control device 5045 may control the drive of the arm 5031 by various well-known control methods such as force control, position control or the like.

For example, when the operator 5067 performs an appropriate operation input via the input device 5047 (including a foot switch 5057), the drive of the arm 5031 is appropriately controlled by the arm control device 5045 in accordance with the operation input, and the position and attitude of the endoscope 5001 may be controlled. With this control, it is possible to move the endoscope 5001 at a distal end of the arm 5031 from an arbitrary position to an arbitrary position, and thereafter fixedly support the same in the position after movement. Note that, the arm 5031 may be operated by a so-called master-slave method. In this case, the arm 5031 may be remotely operated by the user via the input device 5047 installed in a location away from an operating room.

Furthermore, in a case where the force control is applied, the arm control device 5045 may perform so-called power assist control of receiving an external force from the user to drive the actuators of the respective joints 5033a to 5033c so that the arm 5031 moves smoothly according to the external force. Therefore, when the user moves the arm 5031 while directly touching the arm 5031, the arm 5031 may be moved with a relatively light force. Therefore, the endoscope 5001 may be moved more intuitively and by a simpler operation, and the user convenience may be improved.

Here, generally, in the endoscopic surgery, the endoscope 5001 has been supported by a surgeon called a scopist. In contrast, by using the support arm device 5027, the position of the endoscope 5001 may be more reliably fixed without manual operation, so that the image of the surgical site may be stably obtained and the surgery may be performed smoothly.

Note that, the arm control device 5045 is not necessarily provided on the cart 5037. Furthermore, the arm control device 5045 is not necessarily one device. For example, the arm control device 5045 may be provided on each of the joints 5033a to 5033c of the arm 5031 of the support arm device 5027, and a plurality of arm control devices 5045 may cooperate with each other to realize drive control of the arm 5031.

Light Source Device

The light source device 5043 supplies the endoscope 5001 with the irradiation light when imaging the surgical site. The light source device 5043 includes, for example, a white light source including an LED, a laser light source, or a combination thereof. Since output intensity and output timing of each color (each wavelength) may be controlled with a high degree of accuracy in a case where the white light source is formed by the combination of RGB laser light sources, the light source device 5043 may adjust white balance of the captured image. Furthermore, in this case, by irradiating the observation target with the laser light from each of the RGB laser light sources in time division manner and controlling drive of the imaging element of the camera head 5005 in synchronism with irradiation timing, it is possible to capture images corresponding to RGB in time division manner. According to this method, a color image may be obtained without providing a color filter on the imaging element.

Furthermore, the drive of the light source device 5043 may be controlled such that the intensity of the light to be output is changed every predetermined time. By controlling the drive of the imaging element of the camera head 5005 in synchronization with change timing of the light intensity to obtain the images in time division manner and combining the images, an image of a high dynamic range without so-called black defect and halation may be generated.

Furthermore, the light source device 5043 may be configured to be able to supply light of a predetermined wavelength band corresponding to special light observation. In the special light observation, for example, by using wavelength dependency of absorption of light in body tissue, by applying light of a narrower band than that of the irradiation light (that is, white light) at ordinary observation, so-called narrowband imaging is performed in which predetermined tissue such as the blood vessel in the mucosal surface layer and the like is imaged with high contrast. Alternatively, in the special light observation, fluorescent observation for obtaining an image by fluorescence generated by irradiation of excitation light may be performed. In the fluorescent observation, it is possible to irradiate the body tissue with the excitation light to observe the fluorescence from the body tissue (autonomous fluorescent observation), locally inject a reagent such as indocyanine green (ICG) to the body tissue and irradiate the body tissue with the excitation light corresponding to a fluorescent wavelength of the reagent, thereby obtaining a fluorescent image or the like. The light source device 5043 may be configured to be able to supply the narrowband light and/or excitation light supporting such special light observation.

Camera Head and CCU

With reference to FIG. 14, functions of the camera head 5005 and the CCU 5039 of the endoscope 5001 are described in further detail. FIG. 14 is a block diagram illustrating an example of functional configurations of the camera head 5005 and the CCU 5039 illustrated in FIG. 13.

With reference to FIG. 14, the camera head 5005 includes a lens unit 5007, an imaging unit 5009, a drive unit 5011, a communication unit 5013, and a camera head control unit 5015 as functions thereof. Furthermore, the CCU 5039 includes a communication unit 5059, an image processing unit 5061, and a control unit 5063 as functions thereof. The camera head 5005 and the CCU 5039 are connected to each other so as to be able to bidirectionally communicate by a transmission cable 5065.

First, a functional configuration of the camera head 5005 is described. The lens unit 5007 is an optical system provided at a connection to the lens tube 5003. The observation light taken in from the distal end of the lens tube 5003 is guided to the camera head 5005 and is incident on the lens unit 5007. The lens unit 5007 is formed by combining a plurality of lenses including a zoom lens and a focus lens. An optical characteristic of the lens unit 5007 is adjusted such that the observation light is condensed on a light-receiving surface of the imaging element of the imaging unit 5009. Furthermore, the zoom lens and the focus lens are configured such that positions thereof on an optical axis are movable for adjusting magnification and focal point of the captured image.

The imaging unit 5009 includes the imaging element, and is arranged on a subsequent stage of the lens unit 5007. The observation light that passes through the lens unit 5007 is condensed on the light-receiving surface of the imaging element, and the image signal corresponding to the observation image is generated by photoelectric conversion. The image signal generated by the imaging unit 5009 is provided to the communication unit 5013.

As the imaging element that forms the imaging unit 5009, for example, a complementary metal oxide semiconductor (CMOS) type image sensor having a Bayer array capable of performing color imaging is used. Note that, as the imaging element, that capable of supporting the imaging of a high-resolution image of, for example, 4K or more may be used. Since the image of the surgical site at high resolution may be obtained, the operator 5067 may grasp the state of the surgical site in further detail, and may proceed with the surgery more smoothly.

Furthermore, the imaging element forming the imaging unit 5009 includes a pair of imaging elements for obtaining image signals for right eye and left eye corresponding to 3D display. By the 3D display, the operator 5067 may grasp a depth of the living tissue in the surgical site more accurately. Note that, in a case where the imaging unit 5009 is of a multiple plate type, a plurality of systems of lens units 5007 is provided so as to correspond to the respective imaging elements.

Furthermore, the imaging unit 5009 is not necessarily provided on the camera head 5005. For example, the imaging unit 5009 may be provided inside the lens tube 5003 immediately after the objective lens.

The drive unit 5011 includes an actuator and moves the zoom lens and the focus lens of the lens unit 5007 by a predetermined distance along the optical axis under control of the camera head control unit 5015. Therefore, the magnification and focal point of the image captured by the imaging unit 5009 may be appropriately adjusted.

The communication unit 5013 includes a communication device for transmitting and receiving various types of information to and from the CCU 5039. The communication unit 5013 transmits the image signal obtained from the imaging unit 5009 as RAW data to the CCU 5039 via the transmission cable 5065. At that time, it is preferable that the image signal be transmitted by optical communication in order to display the captured image of the surgical site with low latency. At the time of surgery, the operator 5067 performs surgery while observing a state of the affected site with the captured image, so that it is required that a moving image of the surgical site be displayed in real time as much as possible for safer and more reliable surgery. In a case where the optical communication is performed, the communication unit 5013 is provided with a photoelectric conversion module that converts an electric signal into an optical signal. The image signal is converted into the optical signal by the photoelectric conversion module, and then transmitted to the CCU 5039 via the transmission cable 5065.

Furthermore, the communication unit 5013 receives the control signal for controlling drive of the camera head 5005 from the CCU 5039. The control signal includes, for example, the information regarding the imaging condition such as information specifying a frame rate of the captured image, information specifying an exposure value at the time of imaging, and/or information specifying the magnification and focal point of the captured image. The communication unit 5013 provides the received control signal to the camera head control unit 5015. Note that, the control signal from the CCU 5039 may also be transmitted by the optical communication. In this case, the communication unit 5013 is provided with a photoelectric conversion module that converts the optical signal into the electric signal, and the control signal is converted into the electric signal by the photoelectric conversion module, and then provided to the camera head control unit 5015.

Note that, the imaging conditions such as the frame rate, exposure value, magnification, focal point and the like described above are automatically set by the control unit 5063 of the CCU 5039 on the basis of the obtained image signal. That is, the endoscope 5001 is equipped with a so-called auto exposure (AE) function, an auto focus (AF) function, and an auto white balance (AWB) function.

The camera head control unit 5015 controls drive of the camera head 5005 on the basis of the control signal from the CCU 5039 received via the communication unit 5013. For example, the camera head control unit 5015 controls the drive of the imaging element of the imaging unit 5009 on the basis of the information specifying the frame rate of the captured image and/or the information specifying the exposure at the time of imaging. Furthermore, for example, the camera head control unit 5015 appropriately moves the zoom lens and the focus lens of the lens unit 5007 via the drive unit 5011 on the basis of the information specifying the magnification and focal point of the captured image. The camera head control unit 5015 may further have a function of storing information for identifying the lens tube 5003 and the camera head 5005.

Note that, by arranging components such as the lens unit 5007, the imaging unit 5009 and the like in a hermetically sealed structure having high airtightness and waterproofness, the camera head 5005 may have resistance to autoclave sterilization.

Next, a functional configuration of the CCU 5039 is described. The communication unit 5059 includes a communication device for transmitting and receiving various types of information to and from the camera head 5005. The communication unit 5059 receives the image signal transmitted from the camera head 5005 via the transmission cable 5065. At that time, as described above, the image signal may be preferably transmitted by the optical communication. In this case, the communication unit 5059 is provided with a photoelectric conversion module that converts an optical signal into an electric signal corresponding to optical communication. The communication unit 5059 provides the image signal converted into the electric signal to the image processing unit 5061.

Furthermore, the communication unit 5059 transmits a control signal for controlling the drive of the camera head 5005 to the camera head 5005. The control signal may also be transmitted by the optical communication.

The image processing unit 5061 applies various types of image processing to the image signal that is the RAW data transmitted from the camera head 5005. The image processing includes, for example, various types of well-known signal processing such as development processing, high image quality processing (such as band enhancement processing, super-resolution processing, noise reduction (NR) processing, and/or camera shake correction processing), and/or scaling processing (electronic zoom processing). Furthermore, the image processing unit 5061 performs wave detection processing on the image signal for performing AE, AF, and AWB.

The image processing unit 5061 includes a processor such as a CPU, a GPU and the like, and the above-described image processing and wave detection processing may be performed by the processor operating according to a predetermined program. Note that, in a case where the image processing unit 5061 includes a plurality of GPUs, the image processing unit 5061 appropriately divides information regarding the image signal, and performs the image processing in parallel by the plurality of GPUs.

The control unit 5063 performs various controls regarding imaging of the surgical site by the endoscope 5001 and display of the captured image. For example, the control unit 5063 generates the control signal for controlling the drive of the camera head 5005. At that time, in a case where the imaging condition is input by the user, the control unit 5063 generates the control signal on the basis of the input by the user. Alternatively, in a case where the endoscope 5001 has the AE function, AF function, and AWB function, the control unit 5063 appropriately calculates optimal exposure value, focal distance, and white balance in accordance with a result of the wave detection processing by the image processing unit 5061 to generate the control signal.

Furthermore, the control unit 5063 allows the display device 5041 to display the image of the surgical site on the basis of the image signal subjected to the image processing by the image processing unit 5061. At that time, the control unit 5063 recognizes various objects in the surgical site image by using various image recognition technologies. For example, the control unit 5063 may detect a shape, a color and the like of an edge of the object included in the surgical site image, thereby recognizing a surgical tool such as forceps, a specific living-body site, bleeding, mist when using the energy treatment tool 5021 and the like. When allowing the display device 5041 to display the image of the surgical site, the control unit 5063 displays various types of surgery assist information in a superimposed manner on the image of the surgical site using a recognition result. The surgery assist information is displayed in a superimposed manner, and presented to the operator 5067, so that it becomes possible to more safely and reliably proceed with the surgery.

The transmission cable 5065 connecting the camera head 5005 and the CCU 5039 is an electric signal cable supporting communication of electric signals, an optical fiber supporting optical communication, or a composite cable thereof.

Here, in the illustrated example, the communication is performed by wire using the transmission cable 5065, but the communication between the camera head 5005 and the CCU 5039 may be performed wirelessly. In a case where the communication between the both is performed wirelessly, it is not necessary to lay the transmission cable 5065 in the operating room, so that a situation in which movement of medical staffs in the operating room is hindered by the transmission cable 5065 may be solved.

An example of the endoscopic surgery system 5000 to which the technology according to the present disclosure may be applied is described above. Note that, a system to which the technology according to the present disclosure may be applied is not limited to the endoscope system. For example, the technology according to the present disclosure may be applied to another system such as an inspection flexible endoscope system, a microscopic surgery system or the like.

The technology according to the present disclosure may be preferably applied to the endoscope 5001 out of the configuration described above. Specifically, the technology according to the present disclosure may be applied in a case where the image of the surgical site in the body cavity of the patient 5071 captured by the endoscope 5001 is displayed on the display device 5041. By applying the technology according to the present disclosure to the endoscope 5001, it is possible to more reliably decrease the visibility of the moving image noise by performing the NR processing in the time direction using the image N (N is an integer not smaller than 2) frames before in place of the image one frame before as the reference image. Therefore, the operator 5067 may view the image of the surgical site with more reliably decreased visibility of the noise in real time on the display device 5041, and may perform surgery more safely.

Application Example 2

Furthermore, the technology according to the present disclosure may be applied to, for example, a microscopic surgery system. Hereinafter, a microscopic surgery system as an example of the microscope system is described. The microscopic surgery system is a system used for so-called microsurgery performed while observing a minute site of a patient under magnification.

FIG. 15 is a view illustrating an example of a schematic configuration of a microscopic surgery system 5300 to which the technology according to the present disclosure may be applied. With reference to FIG. 15, the microscopic surgery system 5300 includes a microscope device 5301, a control device 5317, and a display device 5319. Note that, in the following description of the microscopic surgery system 5300, a "user" means an arbitrary medical staff who uses the microscopic surgery system 5300 such as an operator, an assistant and the like.

The microscope device 5301 includes a microscope unit 5303 for observing an observation target (surgical site of the patient) under magnification, an arm 5309 that supports the microscope unit 5303 at a distal end thereof, and a base 5315 that supports a proximal end of the arm 5309.

The microscope unit 5303 includes a substantially cylindrical tubular portion 5305, an imaging unit (not illustrated) provided inside the tubular portion 5305, and an operation unit 5307 provided in a partial region on an outer periphery of the tubular portion 5305. The microscope unit 5303 is an electronic imaging microscope unit (so-called video microscope unit) that electronically captures an image by the imaging unit.

A cover glass for protecting the imaging unit inside is provided on an opening surface at a lower end of the tubular portion 5305. Light from the observation target (hereinafter also referred to as observation light) passes through the cover glass to be incident on the imaging unit inside the tubular portion 5305. Note that, a light source of, for example, a light emitting diode (LED) and the like may be provided inside the tubular portion 5305, and at the time of imaging, the observation target may be irradiated with light from the light source via the cover glass.

The imaging unit includes an optical system that condenses the observation light and an imaging element that receives the observation light condensed by the optical system. The optical system is formed by combining a plurality of lenses including a zoom lens and a focus lens, and an optical characteristic thereof is adjusted such that an image of the observation light is formed on a light-receiving surface of the imaging element. The imaging element receives the observation light and photoelectrically converts the same to generate a signal corresponding to the observation light, that is, an image signal corresponding to an observation image. As the imaging element, for example, that including a Bayer array capable of color imaging is used. The imaging element may be various types of well-known imaging elements such as a complementary metal oxide semiconductor (CMOS) image sensor, a charge coupled device (CCD) image sensor or the like. The image signal generated by the imaging element is transmitted to the control device 5317 as RAW data. Here, the transmission of the image signal may be preferably performed by optical communication. At a surgical site, the operator performs surgery while observing a state of an affected site with the captured image, so that it is required that a moving image of the surgical site be displayed in real time as much as possible for safer and more reliable surgical procedure. By transmitting the image signal by the optical communication, the captured image may be displayed with low latency.

Note that, the imaging unit may include a drive mechanism that moves the zoom lens and the focus lens of the optical system along an optical axis. By appropriately moving the zoom lens and the focus lens by the drive mechanism, magnification of the captured image and a focal distance at the time of imaging may be adjusted. Furthermore, the imaging unit may be equipped with various functions that may be generally provided on the electronic imaging microscope unit such as an auto exposure (AE) function, an auto focus (AF) function and the like.

Furthermore, the imaging unit may be configured as a so-called single-plate imaging unit including one imaging element, or may be configured as a so-called multiple-plate imaging unit including a plurality of imaging elements. In a case where the imaging unit is of the multiple-plate type, for example, the image signals corresponding to RGB may be generated by the respective imaging elements, and a color image may be obtained by combining them. Alternatively, the imaging unit may include a pair of imaging elements for obtaining image signals for right eye and left eye corresponding to stereoscopic vision (3D display). By the 3D display, the operator may grasp a depth of living tissue in the surgical site more accurately. Note that, in a case where the imaging unit is of the multiple-plate type, a plurality of optical systems may be provided so as to correspond to the respective imaging elements.

The operation unit 5307 is formed by using, for example, a cross lever, a switch or the like, and is an input means that receives a user operation input. For example, the user may input an instruction to change the magnification of the observation image and the focal distance to the observation target via the operation unit 5307. By appropriately moving the zoom lens and the focus lens by the drive mechanism of the imaging unit according to the instruction, the magnification and focal distance may be adjusted. Furthermore, for example, the user may input an instruction to switch an operation mode (all-free mode and fixed mode to be described later) of the arm 5309 via the operation unit 5307. Note that, in a case where the user wants to move the microscope unit 5303, a mode is assumed in which the user moves the microscope unit 5303 in a state where the user grips the tubular portion 5305. Therefore, the operation unit 5307 is preferably provided in a position where the user may easily operate the same with a finger while gripping the tubular portion 5305 such that the user may operate the same while moving the tubular portion 5305.

The arm 5309 includes a plurality of links (first link 5313a to sixth link 5313f) being rotatably connected to each other by a plurality of joints (first joint 5311a to sixth joint 5311f).

The first joint 5311a has a substantially cylindrical shape, and supports at a distal end (lower end) thereof an upper end of the tubular portion 5305 of the microscope unit 5303 so as to be rotatable around a rotational axis (first axis O1) parallel to a central axis of the tubular portion 5305. Here, the first joint 5311a may be configured such that the first axis O1 coincides with the optical axis of the imaging unit of the microscope unit 5303. Therefore, by rotating the microscope unit 5303 around the first axis O1, it becomes possible to change a visual field so as to rotate the captured image.

The first link 5313a fixedly supports the first joint 5311a at a distal end thereof. Specifically, the first link 5313a is a rod-shaped member having a substantially L shape, and while one side on the distal end side thereof extends in a direction orthogonal to the first axis O1, an end of the one side is connected to the first joint 5311a so as to abut an upper end of an outer periphery of the first joint 5311a. The second joint 5311b is connected to an end of the other side on a proximal end side of the substantially L shape of the first link 5313a.

The second joint 5311b has a substantially cylindrical shape and supports the proximal end of the first link 5313a so as to be rotatable around a rotational axis (second axis O2) orthogonal to the first axis O1. A distal end of the second link 5313b is fixedly connected to a proximal end of the second joint 5311b.

The second link 5313b is a rod-shaped member having a substantially L shape, and while one side on the distal end side thereof extends in a direction orthogonal to the second axis O2, an end of the one side is fixedly connected to the proximal end of the second joint 5311b. The third joint 5311c is connected to the other side on a proximal end side of the substantially L shape of the second link 5313b.

The third joint 5311c has a substantially cylindrical shape and supports the proximal end of the second link 5313b so as to be rotatable around a rotational axis (third axis O3) orthogonal to the first and second axes O1 and O2 at a distal end thereof. A distal end of the third link 5313c is fixedly connected to a proximal end of the third joint 5311c. The microscope unit 5303 may be moved so as to change a position of the microscope unit 5303 in a horizontal plane by rotating the configuration on the distal end side including the microscope unit 5303 around the second axis O2 and the third axis O3. That is, by controlling the rotation around the second axis O2 and the third axis O3, the visual field of the captured image may be moved in the plane.

The third link 5313c is configured such that the distal end side thereof has a substantially cylindrical shape, and the proximal end of the third joint 5311c is fixedly connected to the distal end of the cylindrical shape such that central axes of both of them are substantially the same. A proximal end side of the third link 5313c has a prismatic shape, and the fourth joint 5311d is connected to an end thereof.

The fourth joint 5311d has a substantially cylindrical shape, and supports the proximal end of the third link 5313c at a distal end thereof so as to be rotatable around a rotational axis (fourth axis O4) orthogonal to the third axis O3. A distal end of the fourth link 5313d is fixedly connected to a proximal end of the fourth joint 5311d.

The fourth link 5313d is a rod-shaped member extending substantially linearly, and while extending so as to be orthogonal to the fourth axis O4, an end on the distal end thereof is fixedly connected to the fourth joint 5311d so as to abut a substantially cylindrical side surface of the fourth joint 5311d. The fifth joint 5311e is connected to a proximal end of the fourth link 5313d.

The fifth joint 5311e has a substantially cylindrical shape, and supports at a distal end side thereof the proximal end of the fourth link 5313d so as to be rotatable around a rotational axis (fifth axis O5) parallel to the fourth axis O4. A distal end of the fifth link 5313e is fixedly connected to a proximal end of the fifth joint 5311e. The fourth axis O4 and the fifth axis O5 are the rotational axes capable of moving the microscope unit 5303 in an up-down direction. By rotating the configuration on the distal end side including the microscope unit 5303 around the fourth axis O4 and the fifth axis O5, a height of the microscope unit 5303, that is, a distance between the microscope unit 5303 and the observation target may be adjusted.

The fifth link 5313e is formed by combining a first member having a substantially L shape in which one side extends in a vertical direction and the other side extends in a horizontal direction, and a second member in a rod shape extending vertically downward from a portion extending horizontally of the first member. The proximal end of the fifth joint 5311e is fixedly connected in the vicinity of an upper end of the portion extending vertically of the first member of the fifth link 5313e. The sixth joint 5311f is connected to a proximal end (lower end) of the second member of the fifth link 5313e.

The sixth joint 5311f has a substantially cylindrical shape and supports at a distal end side thereof the proximal end of the fifth link 5313e so as to be rotatable around a rotational axis (sixth axis O6) parallel to the vertical direction. A distal end of the sixth link 5313f is fixedly connected to a proximal end of the sixth joint 5311f.

The sixth link 5313f is a rod-shaped member extending in the vertical direction, and the proximal end thereof is fixedly connected to an upper surface of the base 5315.

A rotatable range of the first joint 5311a to the sixth joint 5311f is appropriately set such that the microscope unit 5303 may move desirably. Therefore, in the arm 5309 having the above-described configuration, motion of total of six-degree freedom of translational three-degree freedom and rotational three-degree freedom may be realized regarding the motion of the microscope unit 5303. In this manner, by configuring the arm 5309 such that the six-degree freedom is realized regarding the movement of the microscope unit 5303, it is possible to freely control the position and attitude of the microscope unit 5303 within the movable range of the arm 5309. Therefore, the surgical site may be observed from any angle, and the surgery may be performed more smoothly.

Note that, the configuration of the arm 5309 illustrated is merely an example, and the number and shapes (lengths) of the links forming the arm 5309, the number and arranged positions of the joints, the directions of the rotational axes and the like may be appropriately designed such that a desired degree of freedom may be realized. For example, as described above, in order to freely move the microscope unit 5303, the arm 5309 is preferably configured with the six-degree freedom, but the arm 5309 may also be configured with a larger degree of freedom (that is, a redundant degree of freedom). In a case where there is the redundant degree of freedom, the arm 5309 may change the attitude of the arm 5309 in a state in which the position and attitude of the microscope unit 5303 are fixed. Therefore, for example, control that is more convenient for the operator may be realized, such as control of the attitude of the arm 5309 so that the arm 5309 does not interfere with an eyesight of the operator who looks at the display device 5319 and the like.

Here, each of the first joint 5311a to the sixth joint 5311f may be provided with an actuator equipped with a drive mechanism such as a motor, an encoder that detects a rotation angle at each joint and the like. Then, drive of each actuator provided on the first joint 5311a to the sixth joint 5311f is appropriately controlled by the control device 5317, so that the attitude of the arm 5309, that is, the position and attitude of the microscope unit 5303 may be controlled. Specifically, the control device 5317 may grasp current attitude of the arm 5309 and current position and attitude of the microscope unit 5303 on the basis of information regarding the rotation angle of each joint detected by the encoder. The control device 5317 calculates a control value (for example, rotation angle, generated torque or the like) for each joint that realizes movement of the microscope unit 5303 according to the operation input from the user by using the grasped information, and drives the drive mechanism of each joint according to the control value. Note that, at that time, a control method of the arm 5309 by the control device 5317 is not limited, and various well-known control methods such as force control, position control or the like may be applied.

For example, when the operator appropriately performs the operation input via an input device not illustrated, the drive of the arm 5309 may be appropriately controlled by the control device 5317 in accordance with the operation input, and the position and attitude of the microscope unit 5303 may be controlled. With this control, it is possible to move the microscope unit 5303 from an arbitrary position to an arbitrary position, and fixedly support this in the position after movement. Note that, as for the input device, in consideration of the convenience of the operator, it is preferable to apply the one that may be operated even if the operator has a surgical tool in his/her hand such as, for example, a foot switch. Furthermore, a contactless operation input may be performed on the basis of gesture detection or line-of-sight detection using a wearable device or a camera provided in an operating room. Therefore, even a user belonging to a clean area may operate a device belonging to an unclean area with a higher degree of freedom. Alternatively, the arm 5309 may be operated in a so-called master slave method. In this case, the arm 5309 may be remotely operated by the user via an input device installed in a place away from the operating room.

Furthermore, in a case where the force control is applied, so-called power assist control of receiving an external force from the user to drive the actuators of the first to sixth joints 5311a to 5311f so that the arm 5309 moves smoothly according to the external force may be performed. Therefore, when the user grips the microscope unit 5303 to directly move the position thereof, the microscope unit 5303 may be moved with a relatively light force. Therefore, the microscope unit 5303 may be moved more intuitively and with a simpler operation, and user convenience may be improved.

Furthermore, the drive of the arm 5309 may be controlled so as to perform a pivot operation. Here, the pivot operation is an operation of moving the microscope unit 5303 so that the optical axis of the microscope unit 5303 is always directed to a predetermined point in space (hereinafter referred to as a pivot point). According to the pivot operation, the same observation position may be observed in various directions, so that observation of the affected site in further detail becomes possible. Note that, in a case where the microscope unit 5303 is configured so as not to be able to adjust a focal distance thereof, it is preferable that the pivot operation is performed in a state in which a distance between the microscope unit 5303 and the pivot point is fixed. In this case, the distance between the microscope unit 5303 and the pivot point may be adjusted to a fixed focal distance of the microscope unit 5303. Therefore, the microscope unit 5303 moves on a hemisphere (schematically illustrated in FIG. 15) having a radius corresponding to the focal distance centered on the pivot point, and a sharp captured image may be obtained even when the observation direction is changed. In contrast, in a case where the microscope unit 5303 is configured to be able to adjust the focal distance thereof, it is possible that the pivot operation is performed in a state in which the distance between the microscope unit 5303 and the pivot point is variable. In this case, for example, the control device 5317 may calculate the distance between the microscope unit 5303 and the pivot point on the basis of information regarding the rotation angle of each joint detected by the encoder, and automatically adjust the focal distance of the microscope unit 5303 on the basis of a calculation result. Alternatively, in a case where the microscope unit 5303 has an AF function, the focal distance may be automatically adjusted by the AF function every time the distance between the microscope unit 5303 and the pivot point is changed by the pivot operation.

Furthermore, each of the first joint 5311*a* to the sixth joint 5311*f* may be provided with a brake that restricts the rotation thereof. The operation of the brake may be controlled by the control device 5317. For example, in a case where it is desired to fix the position and attitude of the microscope unit 5303, the control device 5317 activates the brake of each joint. Therefore, since the attitude of the arm 5309, that is, the position and attitude of the microscope unit 5303 may be fixed without driving the actuator, power consumption may be reduced. In a case where it is desired to move the position and attitude of the microscope unit 5303, the control device 5317 is only required to release the brake of each joint and drive the actuator according to a predetermined control method.

Such a brake operation may be performed in response to an operation input by the user via the operation unit 5307 described above. In a case where the user wants to move the position and attitude of the microscope unit 5303, the user operates the operation unit 5307 to release the brake of each joint. Therefore, the operation mode of the arm 5309 shifts to a mode (all-free mode) in which the rotation at each joint may be freely performed. Furthermore, in a case where the user wants to fix the position and attitude of the microscope unit 5303, the user operates the operation unit 5307 to activate the brake of each joint. Therefore, the operation mode of the arm 5309 shifts to a mode (fixed mode) in which the rotation at each joint is restricted.

The control device 5317 comprehensively controls the operation of the microscopic surgery system 5300 by controlling the operations of the microscope device 5301 and the display device 5319. For example, the control device 5317 controls the drive of the arm 5309 by operating the actuators of the first joint 5311*a* to the sixth joint 5311*f* according to a predetermined control method. Furthermore, for example, the control device 5317 changes the operation mode of the arm 5309 by controlling the operation of the brake of the first joint 5311*a* to the sixth joint 5311*f*. Furthermore, for example, the control device 5317 generates image data for display by applying various types of signal processing to the image signal obtained by the imaging unit of the microscope unit 5303 of the microscope device 5301 and allows the display device 5319 to display the image data. As the signal processing, for example, various types of well-known signal processing such as development processing (demosaic processing), high image quality processing (such as band enhancement processing, super-resolution processing, noise reduction (NR) processing, and/or camera shake correction processing), and/or scaling processing (that is, electronic zoom processing) may be performed.

Note that, communication between the control device 5317 and the microscope unit 5303 and communication between the control device 5317 and the first joint 5311*a* to the sixth joint 5311*f* may be wired communication or wireless communication. In a case of the wired communication, communication using electric signals may be performed, or optical communication may be performed. In this case, a transmission cable used for the wired communication may be configured as an electric signal cable, an optical fiber, or a composite cable thereof depending on a communication method. In contrast, in a case of the wireless communication, it is not necessary to lay the transmission cable in the operating room, so that a situation in which movement of medical staffs in the operating room is hindered by the transmission cable may be solved.

The control device 5317 may be a microcomputer, a control board or the like on which a processor such as a central processing unit (CPU), a graphics processing unit (GPU) and the like are mounted, or the processor and a storage element such as a memory are mixedly mounted. The various functions described above may be realized by the processor of the control device 5317 operating according to a predetermined program. Note that, in the illustrated example, the control device 5317 is provided as a separate device from the microscope device 5301; however, the control device 5317 may be installed inside the base 5315 of the microscope device 5301 to be integrated with the microscope device 5301. Alternatively, the control device 5317 may include a plurality of devices. For example, it is possible that a microcomputer, a control board and the like are arranged on each of the microscope unit 5303 and the first joint 5311*a* to the sixth joint 5311*f* of the arm 5309, and they are connected so as to be able to communicate with each other, so that a function similar to that of the control device 5317 is realized.

The display device 5319 is provided in the operating room, and displays an image corresponding to the image data generated by the control device 5317 under control of the control device 5317. That is, the display device 5319 displays an image of the surgical site captured by the microscope unit 5303. Note that, the display device 5319 may display various types of information regarding the surgery such as physical information of the patient, information regarding a surgical procedure and the like, for example, in place of or together with the image of the surgical site. In this case, the display of the display device 5319 may be appropriately switched by an operation by the user. Alternatively, a plurality of display devices 5319 may be provided, and each of a plurality of display devices 5319 may display the image of the surgical site and various types of information regarding the surgery. Note that, as the display device 5319, various well-known display devices such as a liquid crystal display device, an electro luminescence (EL) display device and the like may be applied.

FIG. 16 is a view illustrating a state of surgery using the microscopic surgery system 5300 illustrated in FIG. 15. FIG. 16 schematically illustrates a state in which an operator 5321 performs surgery on a patient 5325 on a patient bed 5323 by using the microscopic surgery system 5300. Note that, in FIG. 16, for simplicity, the control device 5317 out of the configuration of the microscopic surgery system 5300 is not illustrated, and the microscope device 5301 is illustrated in a simplified manner.

As illustrated in FIG. 2C, at the time of surgery, the image of the surgical site captured by the microscope device 5301 is displayed in an enlarged manner on the display device 5319 installed on a wall surface of the operating room using the microscopic surgery system 5300. The display device 5319 is installed in a position facing the operator 5321, and the operator 5321 performs various procedures on the surgical site such as resection of the affected site, for example, while observing the state of the surgical site by a video displayed on the display device 5319.

An example of the microscopic surgery system 5300 to which the technology according to the present disclosure may be applied is described above. Note that, the microscopic surgery system 5300 is herein described as an example, but a system to which the technology according to the present disclosure may be applied is not limited to such an example. For example, the microscope device 5301 may serve as a support arm device that supports another observation device or another surgical tool in place of the microscope unit 5303 at the distal end thereof. As another observation device described above, for example, an endoscope may be applied. Furthermore, as another surgical tool described above, forceps, tweezers, an insufflation tube for insufflation, an energy treatment tool for incising tissue or sealing the blood vessel by cauterization or the like may be applied. By supporting such observation device and surgical tool with the support arm device, it is possible to fix the position more stably and reduce a burden on the medical staff as compared to a case where the medical staff supports the same manually. The technology according to the present disclosure may be applied to the support arm device that supports such configuration other than the microscope unit.

The technology according to the present disclosure may be preferably applied to the control device 5317 out of the configuration described above. Specifically, the technology according to the present disclosure may be applied in a case where the image of the surgical site of the patient 5325 captured by the imaging unit of the microscope unit 5303 is displayed on the display device 5319. By applying the technology according to the present disclosure to the control device 5317, it is possible to more reliably decrease the visibility of the moving image noise by performing the NR processing in the time direction using the image N (N is an integer not smaller than 2) frames before in place of the image one frame before as the reference image. Therefore, the operator 5321 may view the image of the surgical site with more reliably decreased visibility of the noise in real time on the display device 5319, and may perform surgery more safely.

Note that, the present technology may also have following configurations.

(1)
A medical system provided with:
a light source configured to irradiate an imaging target with light;
an imaging device configured to image reflected light from the imaging target irradiated with the light; and
a noise reduction processing means configured to acquire a plurality of images captured by the imaging device and perform noise reduction processing on one image of interest out of a plurality of the images, in which
the noise reduction processing means uses an image N (N is an integer not smaller than 2) frames before as a reference image.

(2)
The medical system according to (1), in which the medical system is a microscope system or an endoscope system.

(3)
An information processing device provided with:
a noise reduction processing means configured to acquire a plurality of images captured by an imaging device that images reflected light from an imaging target irradiated with light, and perform noise reduction processing on one image of interest out of a plurality of the images, in which
the noise reduction processing means uses an image N (N is an integer not smaller than 2) frames before as a reference image.

(4)
The information processing device according to (3), further provided with:
a motion estimation means configured to calculate a motion vector between a plurality of the images on the basis of a feature amount in the image, in which
in a case where the noise reduction processing is performed on the image of interest, the noise reduction processing means performs the noise reduction processing by using at least one of the image N frames before or an image one frame before as the reference image according to magnitude of the motion vector.

(5)
The information processing device according to (4), in which
the noise reduction processing means
performs, in a case where the magnitude of the motion vector is equal to or larger than a predetermined threshold, the noise reduction processing using the image one frame before as the reference image, and
performs, in a case where the magnitude of the motion vector is smaller than a predetermined threshold, the noise reduction processing using the image N frames before as the reference image.

(6)
The information processing device according to (4), further provided with:
a reference image selection means configured to combine the image N frames before and the image one frame before with weight according to the magnitude of the motion vector to create a combined reference image, in which
the noise reduction processing means performs the noise reduction processing using the combined reference image.

(7)
The information processing device according to (3), in which N is an integer satisfying following expression (1):

$$\text{(time length between frames)} \times N \leq 100 \text{ ms} \quad \text{expression (1)}$$

(8)
An information processing method provided with:
a noise reduction processing step of acquiring a plurality of images captured by an imaging device that images reflected light from an imaging target irradiated with light, and performing noise reduction processing on one image of interest out of a plurality of the images, in which
the noise reduction processing step uses an image N (N is an integer not smaller than 2) frames before the image of interest as a reference image.

Although the embodiments and variation of the present disclosure are described above, the technical scope of the present disclosure is not limited to the above-described embodiments and variation, and various modifications may be made without departing from the gist of the present disclosure. Furthermore, the components of different embodiments and variation may be appropriately combined.

For example, the NR processing in the first embodiment uses not the input image but the output image as the reference image, and is referred to as the cyclic NR processing; however, there is no limitation and the input image may be used as the reference image.

Furthermore, in each embodiment, when the NR processing in the time direction is performed, the NR processing in a spatial direction may be performed in parallel.

Furthermore, in FIG. 7, the NR unit 412 and the motion estimation unit 416 are described as separate functional units; however, there is no limitation, and for example, a motion estimation function may be included in the NR unit 412.

Furthermore, for example, the NR processing may be performed in consideration of information such as a noise amount of the special light image known from a signal amplification factor of the IR imager.

Furthermore, in the first embodiment, in a case where the NR processing is performed in the time direction, the image two frames before is always used as the reference image; however, there is no limitation, and for example, a case where the image one frame before is used regardless of the motion in the image may be included. That is, in a case where the NR processing is performed in the time direction, it is not always necessary to use the image N (N is an integer not smaller than 2) or more frames before as the reference image; it is only required to do so at least at times.

Furthermore, for example, in a case where the motion estimation is performed in units of blocks and a motion estimation result is used in the NR processing, this may be converted into units of pixels to be used.

Furthermore, the effects in each embodiment and variation of this specification are illustrative only and are not limitative; there may also be another effect.

REFERENCE SIGNS LIST

1 Medical system
2 Light source
3 Imaging device
4 Information processing device
5 Display device
9 Imaging target
41 Processing unit
42 Storage unit
411 Acquisition unit
412 NR unit
413 Reference image selection unit
414 Reference image storage control unit
415 Display control unit
416 Motion estimation unit
421 Storage unit for even-numbered frame
422 Storage unit for odd-numbered frame
423 Storage unit for all frames

The invention claimed is:

1. A medical system, comprising:
a light source configured to irradiate an imaging target with light;
an imaging device configured to capture a plurality of images based on reflected light from the imaging target; and
a central processing unit (CPU) configured to:
acquire the plurality of images from the imaging device, wherein the acquired plurality of images includes an image of interest and at least one even-numbered image;
determine that a frame number of the image of interest is an even number;
select, based on the determination that the frame number of the image of interest is the even number, a reference image from the at least one even-numbered image, wherein
the reference image is an image that is N frames before the image of interest, and
N is an integer that is one of equal to two or greater than two; and
perform a noise reduction process on the image of interest based on the reference image.

2. The medical system according to claim 1, wherein the medical system is a microscope system or an endoscope system.

3. An information processing device, comprising:
a central processing unit (CPU) configured to:
acquire a plurality of images from an imaging device, wherein
the imaging device captures the plurality of images based on reflected light from an imaging target, and
the plurality of images includes an image of interest and at least one even-numbered image;
determine that a frame number of the image of interest is an even number;
select, based on the determination that the frame number of the image of interest is the even number, a reference image from the at least one even-numbered image, wherein
the reference image is an image that is N frames before the image of interest, and
N is an integer that is one of equal to two or greater than two; and
perform a noise reduction process on the image of interest based on the reference image.

4. The information processing device according to claim 3, wherein the CPU is further configured to:
calculate a motion vector between the plurality of images;
determine a weight associated with the motion vector based on a magnitude of the motion vector;
combine the image N frames before the image of interest and an image one frame before the image of interest to create a combined reference image, wherein the image N frames before the image of interest and the image one frame before the image of interest are combined based on the determined; and
perform the noise reduction process based on the combined reference image.

5. The information processing device according to claim 3, wherein N satisfies following expression (1):

$$(\text{Time length between frames}) \times N \leq 100 \text{ ms} \ldots \quad \text{expression (1)}.$$

6. The information processing device according to claim 3, wherein the CPU is further configured to:
calculate a motion vector between the plurality of images based on a feature amount in each image of the plurality of images;
determine that a magnitude of the motion vector is smaller than a threshold; and
select the reference image based on the determination that the magnitude of the motion vector is smaller than the threshold.

7. An information processing method, comprising:
acquiring a plurality of images from an imaging device, wherein
the imaging device captures the plurality of images based on reflected light from an imaging target, and
the plurality of images includes an image of interest and at least one even-numbered image;
determining that a frame number of the image of interest is an even number;
selecting, based on the determination that the frame number of the image of interest is the even number, a reference image from the at least one even-numbered image, wherein
the reference image is an image that is N frames before the image of interest, and
N is an integer that is one of equal to two or greater than two; and
performing a noise reduction process on the image of interest based on the reference image.

* * * * *